(12) United States Patent
Edoga et al.

(10) Patent No.: US 7,201,747 B2
(45) Date of Patent: Apr. 10, 2007

(54) SURGICAL INSTRUMENT POSITIONING SYSTEM AND METHOD OF USE

(75) Inventors: John K Edoga, Morristown, NJ (US); Thierry Richard, Florham Park, NJ (US)

(73) Assignee: Edrich Vascular Devices, Inc., Morristown, NJ (US)

( * ) Notice: Subject to any disclaimer, the term of this patent is extended or adjusted under 35 U.S.C. 154(b) by 114 days.

(21) Appl. No.: 10/690,291

(22) Filed: Oct. 21, 2003

(65) Prior Publication Data

US 2004/0133078 A1 Jul. 8, 2004

Related U.S. Application Data

(60) Provisional application No. 60/419,949, filed on Oct. 21, 2002, provisional application No. 60/452,148, filed on Mar. 5, 2003, provisional application No. 60/476,497, filed on Jun. 6, 2003.

(51) Int. Cl.
  *A61B 17/00* (2006.01)
(52) U.S. Cl. ........................................ 606/1
(58) Field of Classification Search ............... 600/102, 600/204, 227–234; 604/174, 177; 606/1
  See application file for complete search history.

(56) References Cited

U.S. PATENT DOCUMENTS

| | | | |
|---|---|---|---|
| 605,715 | A | 6/1898 | Hohmann |
| 2,493,598 | A | 1/1950 | Rozek |
| 3,762,401 | A | 10/1973 | Tupper |
| 4,380,999 | A | 4/1983 | Healy |
| 4,416,664 | A | 11/1983 | Womack |
| 4,617,916 | A | 10/1986 | LeVahn et al. |
| 4,621,619 | A | 11/1986 | Sharpe |
| 4,805,599 | A | 2/1989 | Ray |
| 5,020,195 | A | 6/1991 | LeVahn |

(Continued)

FOREIGN PATENT DOCUMENTS

DE  23 62947 A1  6/1975

(Continued)

OTHER PUBLICATIONS

U.S. Appl. No. 08/519,130, filed Aug. 24, 1995, Edoga.

*Primary Examiner*—Linda C. M. Dvorak
*Assistant Examiner*—Pete Vrettakos
(74) *Attorney, Agent, or Firm*—Lerner, David, Littenberg, Krumholz & Mentlik, LLP

(57) ABSTRACT

A positioning system for use during surgical procedures comprising a belt assembly adapted to be positioned about a bodily surface of a patient. The belt assembly may comprise a single module, or a first module adapted to be attached to a second module. The modules may be adapted to permit attachment of a surgical instrument thereto. The modules may also include cushioned undersides. The system may also comprise a surgical instrument retention system including a saddle adapted to be positioned on a surgical instrument, straps adapted to secure the saddle to the surgical instrument, and a pulley cord coupled to the saddle so as to selectively position the surgical instrument upon movement of the pulley cord. The modules may also include an accessory adapted to fit securely within shaped openings formed therein. The accessory may comprise a base having a locking apparatus for locking a medical device to the base.

24 Claims, 14 Drawing Sheets

U.S. PATENT DOCUMENTS

| | | |
|---|---|---|
| 5,025,780 A | 6/1991 | Farley |
| 5,183,033 A | 2/1993 | Wilk |
| 5,224,680 A | 7/1993 | Greenstein et al. |
| 5,231,974 A | 8/1993 | Giglio et al. |
| 5,271,745 A | 12/1993 | Fentress et al. |
| 5,334,186 A | 8/1994 | Alexander |
| 5,337,736 A | 8/1994 | Reddy |
| 5,372,147 A | 12/1994 | Lathrop, Jr. et al. |
| 5,375,588 A | 12/1994 | Yoon |
| 5,379,758 A | 1/1995 | Snyder |
| 5,415,159 A | 5/1995 | Ortiz et al. |
| 5,490,819 A | 2/1996 | Nicholas et al. |
| 5,704,900 A | 1/1998 | Dobrovolny et al. |
| 5,728,047 A * | 3/1998 | Edoga .................... 600/227 |
| 5,897,087 A | 4/1999 | Farley |
| 6,058,323 A | 5/2000 | Lemelson |
| 6,113,577 A | 9/2000 | Hakky et al. |
| 6,221,082 B1 | 4/2001 | Marino et al. |

FOREIGN PATENT DOCUMENTS

| | | |
|---|---|---|
| GB | 2223410 | 8/1988 |

* cited by examiner

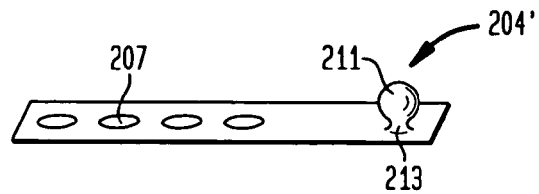
FIG. 7A
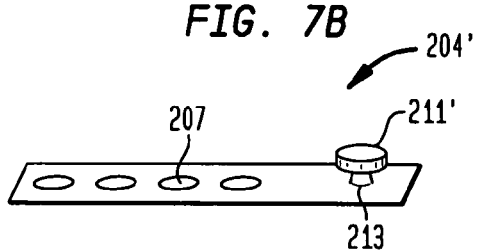
FIG. 7B
FIG. 8
FIG. 9
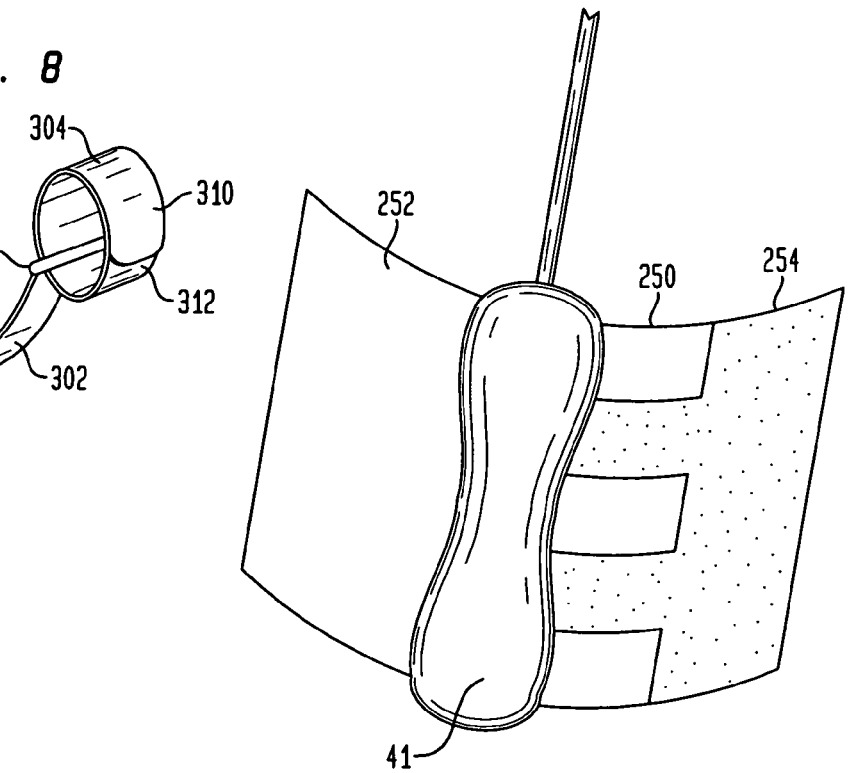

US 7,201,747 B2

SURGICAL INSTRUMENT POSITIONING SYSTEM AND METHOD OF USE

CROSS REFERENCE TO RELATED APPLICATIONS

The present invention relates to U.S. Provisional Patent Application Ser. No. 60/419,949, filed Oct. 21, 2002, U.S. provisional application Ser. No. 60/452,148, filed Mar. 5, 2003, and U.S. Provisional Application Ser. No. 60/476,497 filed Jun. 6, 2003, the disclosures of which are hereby incorporated herein by reference.

BACKGROUND OF THE INVENTION

The present invention is directed towards improvements in the systems of the type described in U.S. Pat. No. 5,728,047 issued to Edoga, one of the present inventors, the disclosure of which is incorporated herein by reference. In U.S. Pat. No. 5,728,047, there is provided a surgical instrument positioning system including a belt assembly positionable about the body of a patient which may be utilized during surgical procedures to assist with tasks previously performed by surgeons. Many of these tasks may be considered "robotic."

For example, laparoscopic cholecystectomy, i.e. the removal of the gallbladder, is typically performed by at least two surgeons. An assistant surgeon provides retraction of the right lobe of the liver by grasping the upper portion of the gallbladder using a ratcheted grasper and pushes the liver forward and to the right. Depending on the operating surgeon's preference, the assistant surgeon either also provides additional traction on the gallbladder by grasping the portion of the gallbladder which leads to the bile ducts or he or she holds the laparoscope. The need to use at least two surgeons makes this procedure unnecessarily costly.

Laparoscopic Nissen fundoplication, i.e., the repair of hiatal hernias and the creation of a valve to check acid reflux from the stomach into the esophagus, is currently performed by at least three surgeons, increasing costs even more. The first assistant surgeon usually holds the laparoscope and also provides the needed traction on the stomach and esophagus while the second assistant surgeon retracts the lateral segment of the left lobe of the liver, in most cases, using a fan retractor.

Besides the increase in costs associated with the need for additional surgeons to mechanically hold surgical instruments in place, problems can also arise during the surgical procedure due to a number of human factors. These problems may include the surgeon becoming fatigued or distracted while trying to hold the instrument in a fixed position, or the surgeon unintentionally permitting the instrument to drift from its original position due to a lack of visual reinforcement of the instrument's position within the patient as the surgeon holding the retractor rarely gets a chance to see the retractor position, especially during the critical stages of the procedures. Moreover, the presence of additional surgeons about the patient can interfere with the operative field and the arm movements of the lead surgeon.

There have been a number of attempts to provide positioning systems for holding retractors and other surgical instruments in a fixed position so as to eliminate the need for human involvement. One example provides for a "stepped" surgical retractor including a ladder-like support which is attached via a universal clamp to the operating table and projects vertically upwardly with respect to the operating table. Although devices of this type eliminate the need for a surgeon to hold the retractor in a fixed position, the support structure of the device can interfere with the arms of the surgeon due to its vertical projection into the operative field. It may also press against the body of a wide or obese patient and may lead to pressure ulcers of the skin.

Other retractor or positioning systems provide mechanical arm devices which are clamped to the side of the operating table and employ a pivoting robotic arm which extends horizontally over the table and patient. These systems also suffer from problems in that they are located in the operative area above the patient and can interfere with the movements of the surgeon. These devices can also be cumbersome and difficult to use. Furthermore, such systems are relatively expensive, especially when provided with hydraulic or motor-assisted lifting mechanisms.

The surgical instrument positioning system developed by the present inventors and disclosed in U.S. Pat. No. 5,728,047 provided great advancements over the prior art. For example, it provided a positioning system for use during surgical procedures, such as during laparoscopic surgery, which was relatively simple to use, inexpensive, and which solved the problems associated with the use of assistant surgeons and positioning systems which interfered with the surgeon. However, it has been discovered that a positioning system of the type disclosed in U.S. Pat. No. 5,728,047 would provide a greater benefit if the positioning system were operable in two planes instead of a single plane. It would also be beneficial if the positioning system provided the ability to secure a retractor or other implement while permitting selective rotational adjustment of the implement. Height adjustment and stabilization of the implement would also be beneficial.

SUMMARY OF THE INVENTION

The aforementioned shortcomings of prior art instrument positioning systems, and others not specifically listed, have been addressed by the present invention, which in one embodiment comprises a belt assembly adapted to be positioned about a bodily surface of a patient. The belt assembly may include a first module adapted to be attached to a second module, wherein at least one of the modules is adapted to permit attachment of a surgical instrument thereto.

In another embodiment, the positioning system comprises a belt assembly positionable about a bodily surface of a patient. The belt assembly may further comprise a platform and a surgical instrument retention system. The surgical instrument retention system may comprise a saddle adapted to be positioned on a surgical instrument, straps adapted to secure the saddle to the surgical instrument, and a pulley cord coupled to the saddle so as to selectively position the surgical instrument upon movement of the pulley cord. The surgical instrument retention system may also be adapted to restrain movement of the surgical instrument.

In another embodiment, a retention system for retaining a surgical instrument may comprise a saddle adapted to be positioned on a surgical instrument, straps adapted to secure the saddle to the surgical instrument, and a pulley cord coupled to the saddle so as to selectively position the surgical instrument upon movement of the pulley cord.

The present invention may also be viewed as providing a method of securing a surgical instrument for use during surgical procedures in which an opening is formed in a patient. The method may comprise inserting a distal portion of the surgical instrument into the opening formed in the patient, strapping a saddle to a proximal portion of the surgical instrument so rotation of the surgical instrument relative to the saddle is inhibited, and securing the saddle to a belt assembly positioned on a bodily surface of the patient by attaching a pulley cord secured to the saddle to the belt assembly.

In yet another embodiment, the instrument positioning system for use during surgical procedures may comprise a belt assembly adapted to be positioned about a bodily surface of a patient where the belt assembly comprises a platform having a shaped opening for receiving an accessory. This embodiment may also include an accessory adapted to fit securely within said shaped opening. The accessory may comprise a base having a locking apparatus for locking a medical device to the base.

In a still further embodiment, the positioning system for use during surgical procedures may comprise a belt assembly positionable about a bodily surface of a patient. The belt assembly may comprise a platform having a first side and a second side. The first side may be adapted to permit attachment of a surgical instrument to it and the second side may include a cushion coupled to it.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

In regard to the drawings,

FIGS. 7A and 7B are perspective views of straps forming portions of the surgical instrument positioning system in accordance with certain embodiments of the present invention;

FIG. 8 is a perspective view of a securement strap forming a portion of the surgical instrument positioning system in accordance with certain embodiments of the present invention;

FIG. 9 is a perspective view of a wrap forming a portion of the surgical instrument positioning system in accordance with certain embodiments of the present invention;

DETAILED DESCRIPTION

Figure 1:
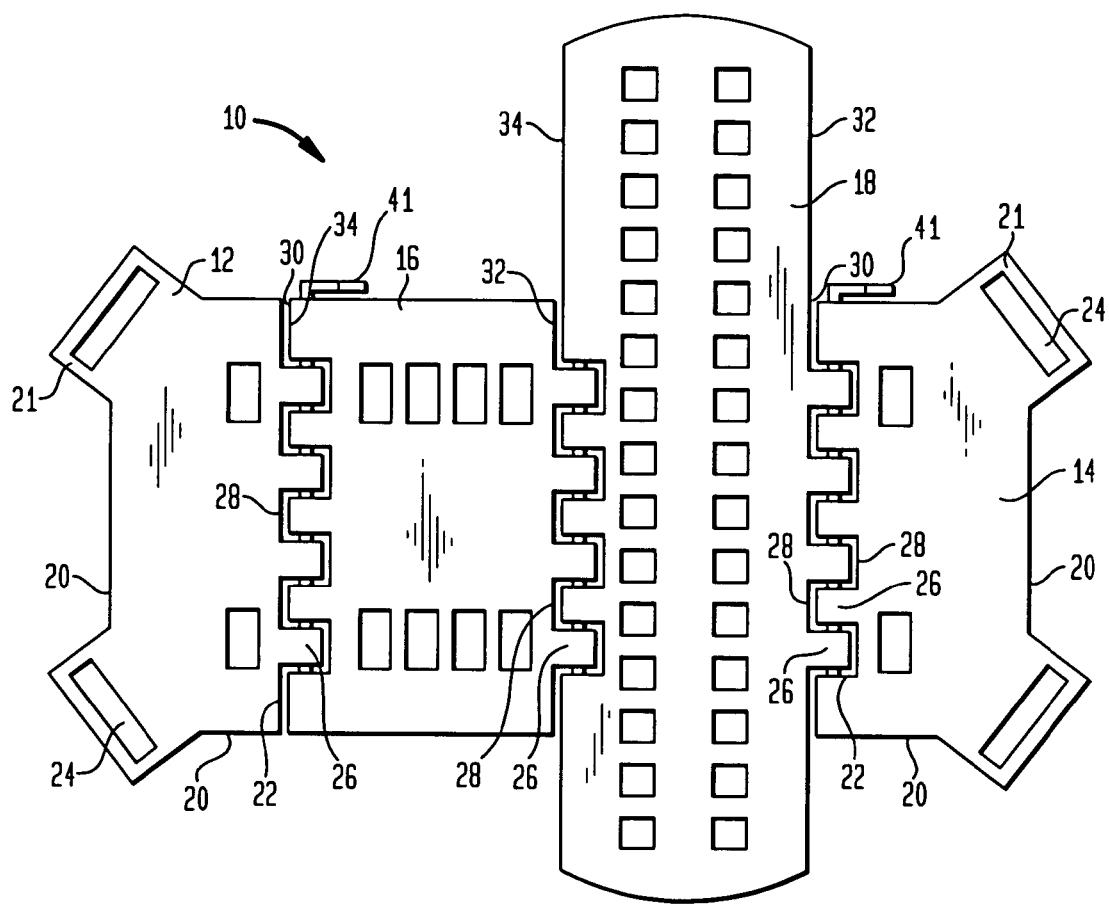
FIG. 1 is a top plan view of a surgical instrument positioning system in accordance with one embodiment of the present invention.

In the following is described the embodiments of the surgical instrument positioning system and method of use of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

Referring to FIG. 1, a belt assembly in accordance with a first embodiment of the present invention is generally designated as element 10. In this embodiment, belt assembly 10 includes a first end module 12 and a second end module 14, with an extension module 16 and a support module 18 therebetween. Each of the modules 12, 14, 16, 18 is constructed so as to be generally planar. As depicted in FIG. 1, the modules 10, 12, 14, 16, 18 may be arranged in series such that the first end module 12 is adjacent the extension module 16 which is adjacent the support module 18 which is adjacent the second end module 14. Numerous additional modules may also be added to comprise the belt assembly 10, depending on the girth of the patient and the relative sizes of the modules.

The first end module 12 and second end module 14 may be constructed and oriented so as to be mirror images of each other when the belt assembly 10 is fully assembled. Each includes an exterior edge 20 and an interior edge 22. The exterior edges 20 form three sides of the end modules 12, 14 and partially surround support protrusions 21 extending outwardly from the first end module 12 and second end module 14. Each of the support protrusions includes elongated openings 24 for attachment of securement straps 300 (FIG. 3), as will be discussed hereinafter. The interior edges 22 of the end modules 12, 14 each form ribbed members 26 separated by recessed areas 28. The ribbed members 26 and recessed areas 28 alternate to form one section of a hinge 30, to which additional modules, for example extension module 16 or support module 18 may be attached.

Each of the extension modules 16 and the support modules 18 include a first edge 32 and a second edge 34. As with the interior edges 22 of the end modules 12, 14, the first and second edges 32, 34 of the extension module 16 and support module 18 each include portions forming ribbed members 26 separated by recessed areas 28. The ribbed members 26 and recessed members 28 of each module 12, 14, 16, 18 are formed such that each is in registration such that hinges 30 are formed when the members 26, 28 of any two modules 12, 14, 16, 18 are placed adjacent to each other.

Figure 2:
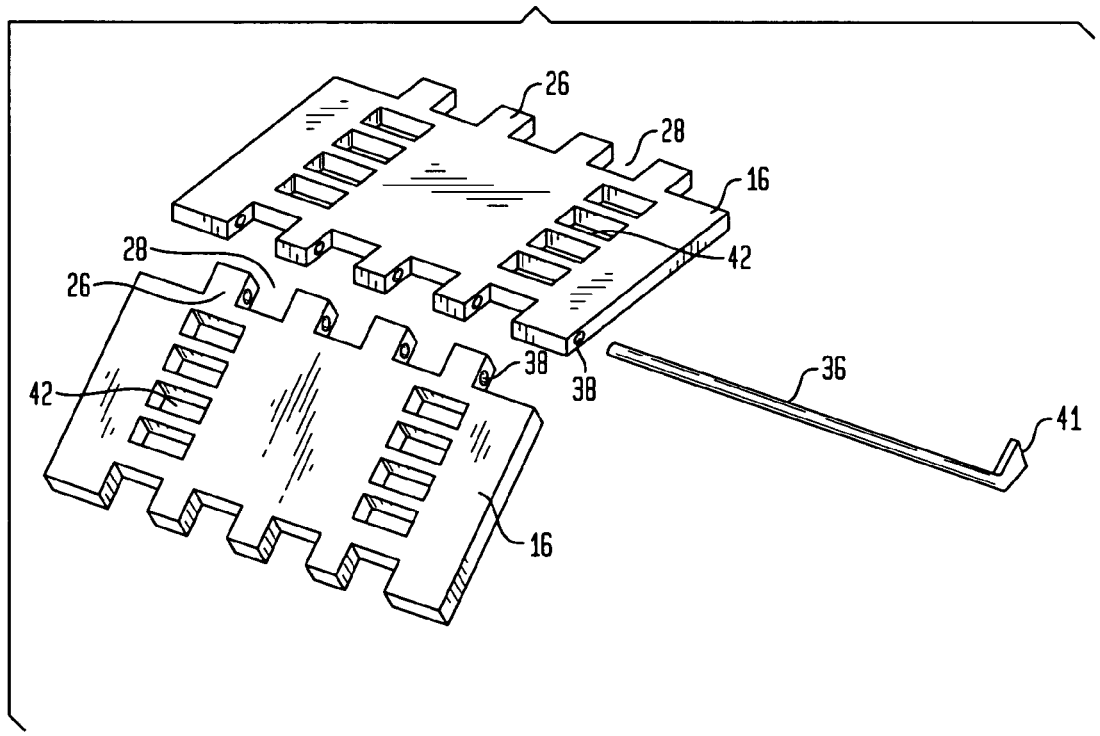
FIG. 2 is an exploded perspective view of portions of a surgical instrument positioning system in accordance with one embodiment of the present invention.

As is shown in FIG. 2, which depicts two extension modules 16 in an exploded perspective view, a suitably sized pin 36 may be driven through a series of apertures 38 provided through each of the ribbed members 26 to attach two modules 12, 14, 16, 18 together, thus completing hinge 30. The pin 36 may include a handle 41 at its distal end to assist with insertion, to prevent the pin from being inserted too far, and to assist with removal.

In a typical device as shown in FIG. 1, the interior edge 22 of the second end module 14 is hinged with the first edge 32 of support member 18. The second edge 34 of support member 18 is hinged with the first edge 32 of extension member 16. Finally, second edge 34 of extension member 16 is hinged with the interior edge 22 of first end module 12. Each of these hinges may be designed with removable pins 36, as shown between modules 12 and 16, or may be provided with permanently installed pins as shown between modules 16 and 18, where no handle 41 is provided to facilitate removal of the pin.

Figure 3:
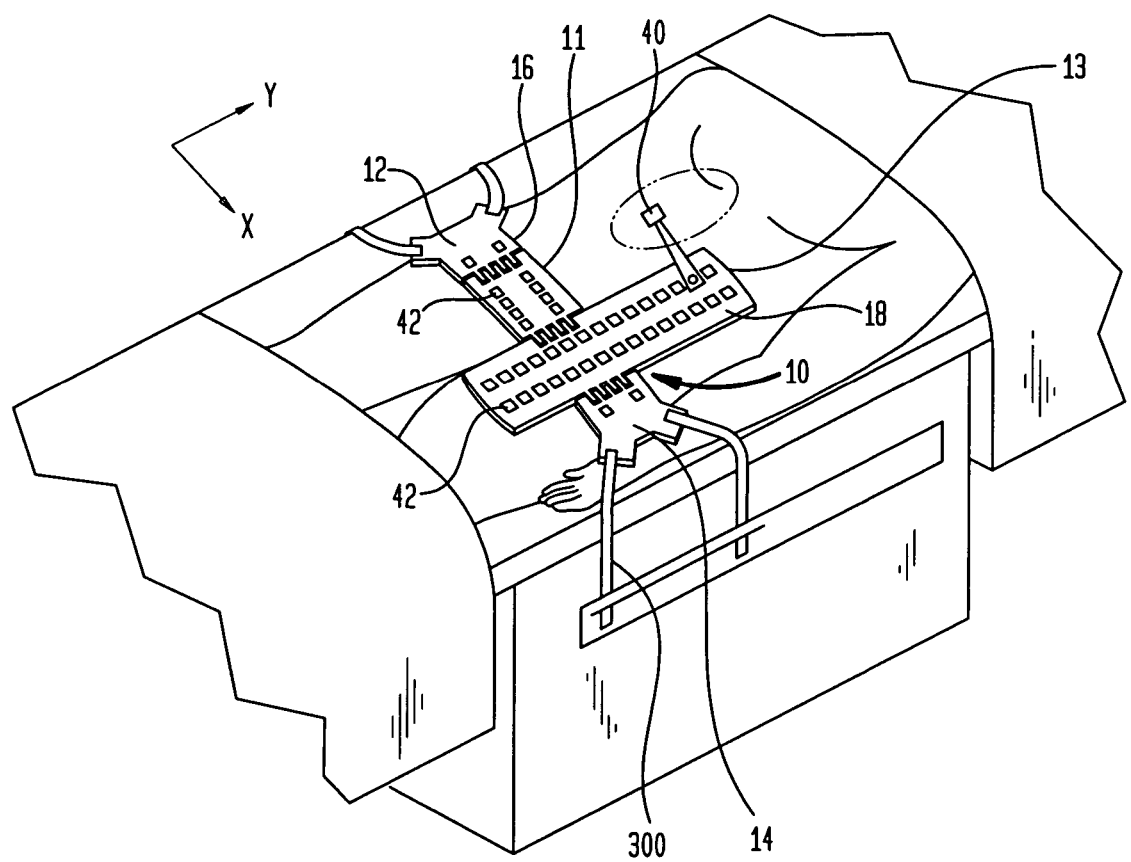
FIG. 3 is a perspective view of a surgical instrument positioning system in accordance with one embodiment of the present invention assembled and in-use on a patient.

It will be appreciated that the extension module 16 and the support module 18 may be provided in alternate configurations from the basic arrangement shown in FIG. 1. Notwithstanding, in this typical arrangement the support module 18 will be on the left hand side of a patient laying in a supine position, as shown in FIG. 3. Of course, the belt assembly 10 may also be arranged such that the support module 18 may be on the patient's right side, or near the center. Additional extension modules 16 may also be provided to account for the girth of a particular patient.

As shown in FIG. 3, for average sized adults, the belt assembly 10 is typically placed with its cephalad edge 11 at the level of the patient's hips. The belt assembly 10 may also be placed slightly higher on the patient's body for patients in the modified lithotomy position.

While the multi-module belt assembly 10 shown in FIG. 1 typically includes four modules 12, 14, 16, 18, this setup is intended to be a basic setup for typically sized individuals. Greater or fewer extension members 16 may also be provided depending on the girth of the patient and the scale of the modules. For obese individuals or where smaller scaled modules are used, multiple extension members 16 may be utilized. As will be detailed hereinafter, a single-section belt assembly, or platform, may also be provided.

The design of the belt assembly 10 works in generally the same manner as the system described in U.S. Pat. No. 5,728,047, incorporated herein by reference. In that regard, the belt assembly 10 is utilized to assist a surgeon in performing "robotic" tasks during medical procedures. FIG. 3 depicts an example of the belt assembly 10 being utilized to assist with a surgical procedure upon a patient. While the system described in U.S. Pat. No. 5,728,047 was best utilized for retracting organs along the x-axis shown in FIG. 3, the present invention may be used to retract organs along both the x and y-axes. As shown in FIG. 3, the support member 18 may be placed such that it extends from the abdomen of a patient up towards the individuals chest. A surgical instrument, such as a retractor 40, may be placed in communication with the support module 18 so as to retract an organ in either the x or y direction. The connection of the surgical instrument may be by any of the means disclosed herein (see, for example, FIGS. 10A through 10I, and related text) or otherwise known in the art.

It will be appreciated that for purposes of this invention, the surgical instrument will typically be referred to as a retractor 40. However, it is to be understood that a wide variety of surgical instruments may be utilized. Where specialized surgical instruments may provide a benefit for certain embodiments, the embodiments have been described with such specialized instruments noted.

Although the support module 18 is generally used to hold the retractor 40, it will be appreciated that each of the modules 12, 14, 16, 18 may be provided with holes 42 which permit attachment of such retractors 40. Thus, a retractor 40 may also be attached to the extension module 16, or either end module 12, 14. When attached to extension module 16, or either end module 12,14, the retractor 40 is best suited for retraction along the x-axis. As previously discussed, it will be appreciated that the belt assembly 10 may be provided with any combination of supports disclosed herein, for example, those disclosed in FIGS. 10A through 10I.

Figure 4A:
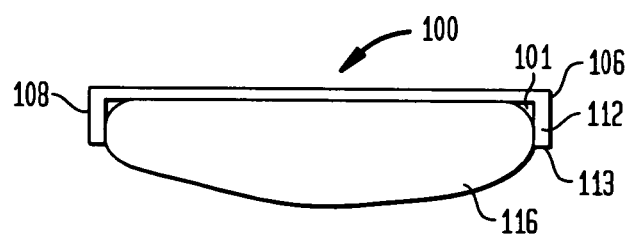
FIG. 4A is a cross-sectional view of the surgical instrument positioning system of FIG. 4.
Figure 4:
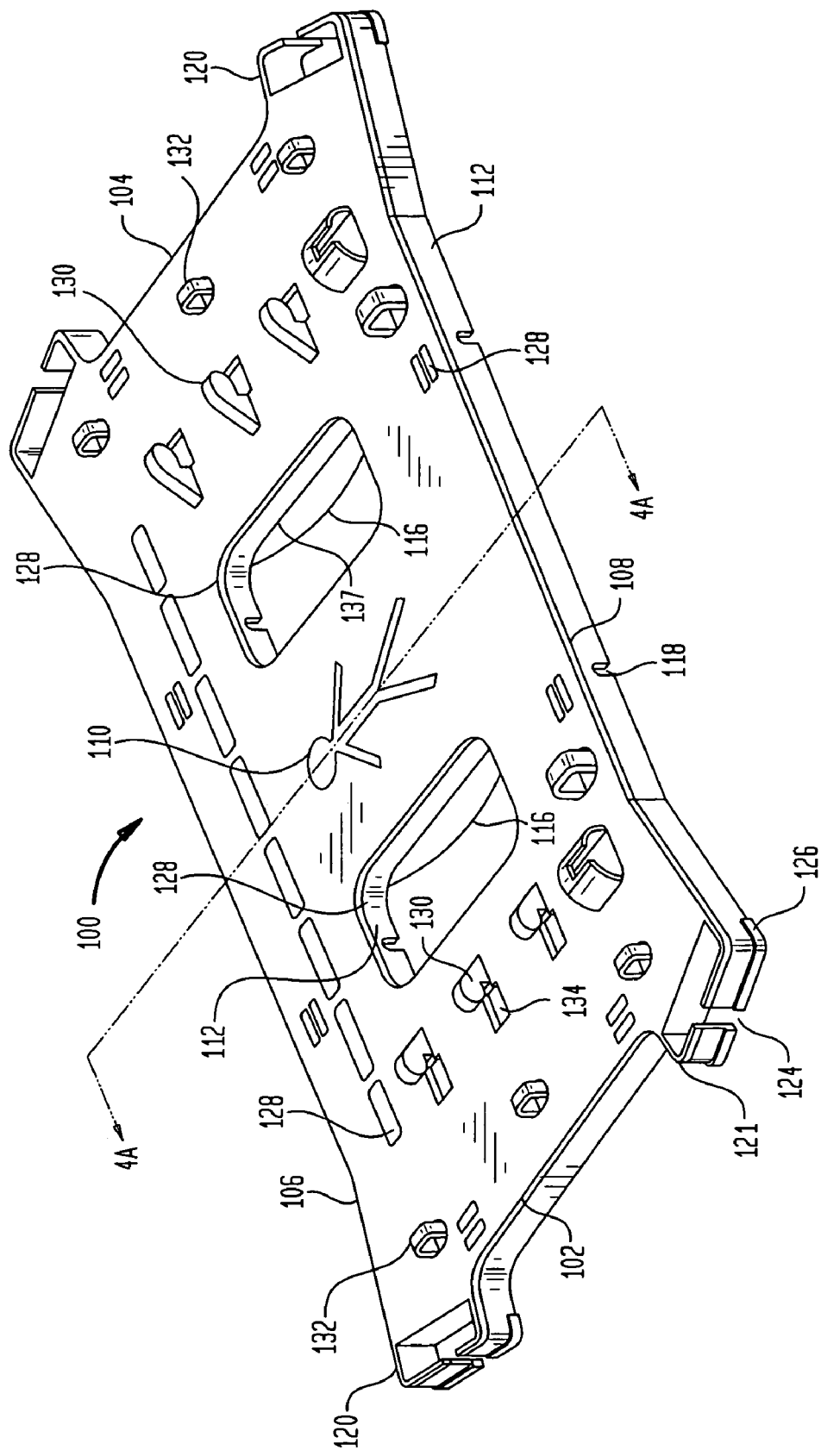
FIG. 4 is a perspective view of a surgical instrument positioning system in accordance with one embodiment of the present invention.

FIG. 4 depicts a belt assembly in accordance with a second embodiment of the present invention, generally designated as element 100. Although features of the belt assemblies and accessories which may be used with the belt assemblies 10, 100 may be described in conjunction with a particular embodiment, it is to be understood that many of the features and each of the accessories may be applied interchangeably to either the single panel belt assembly 100 or multiple panel belt assembly 10.

Belt assembly 100 is formed from a single piece of flexible material, such as plastic, rather than from multiple modules. The belt assembly 100 includes first side edge 102 and second side edge 104. Between the two side edges 102, 104 are a cephalad edge 106 and a caudad edge 108. The four edges 102, 104, 106, 108 combine to form a generally rectangular and flat belt assembly 100. An orientation FIG. 110, such as a depiction of a prone body, may be provided to insure that the medical staff orients the belt assembly 100 correctly. The orientation figure depicted in FIG. 4 directs the belt's assembly in the proper position for upper abdominal operations. Depending on the application, however, it may be desirable to mount the cephalad edge 106 towards the patient's feet, such as laparoscopic appendectomy or laparoscopic pelvic operations.

As shown in FIG. 4a, a cross-sectional view of the belt assembly 100 of FIG. 4 taken along section lines 4A-4A, the edges 102, 104, 106, 108 may include a skirt 112 extending downwardly therefrom. The skirt 112 is preferably formed monolithically with the belt assembly 100 and is typically the same thickness. Within the limits of the skirted area beneath the belt assembly 100 is a void 101. The voided area 101 may be reinforced with structural ribs (not shown) to prevent unwanted flexing of the belt assembly 100. Notwithstanding, in order to permit some flexibility of the belt assembly 100, the skirt 112 may be provided with notches 118 (FIG. 4), selectively placed to allow bending of the belt assembly 100.

Figure 5:
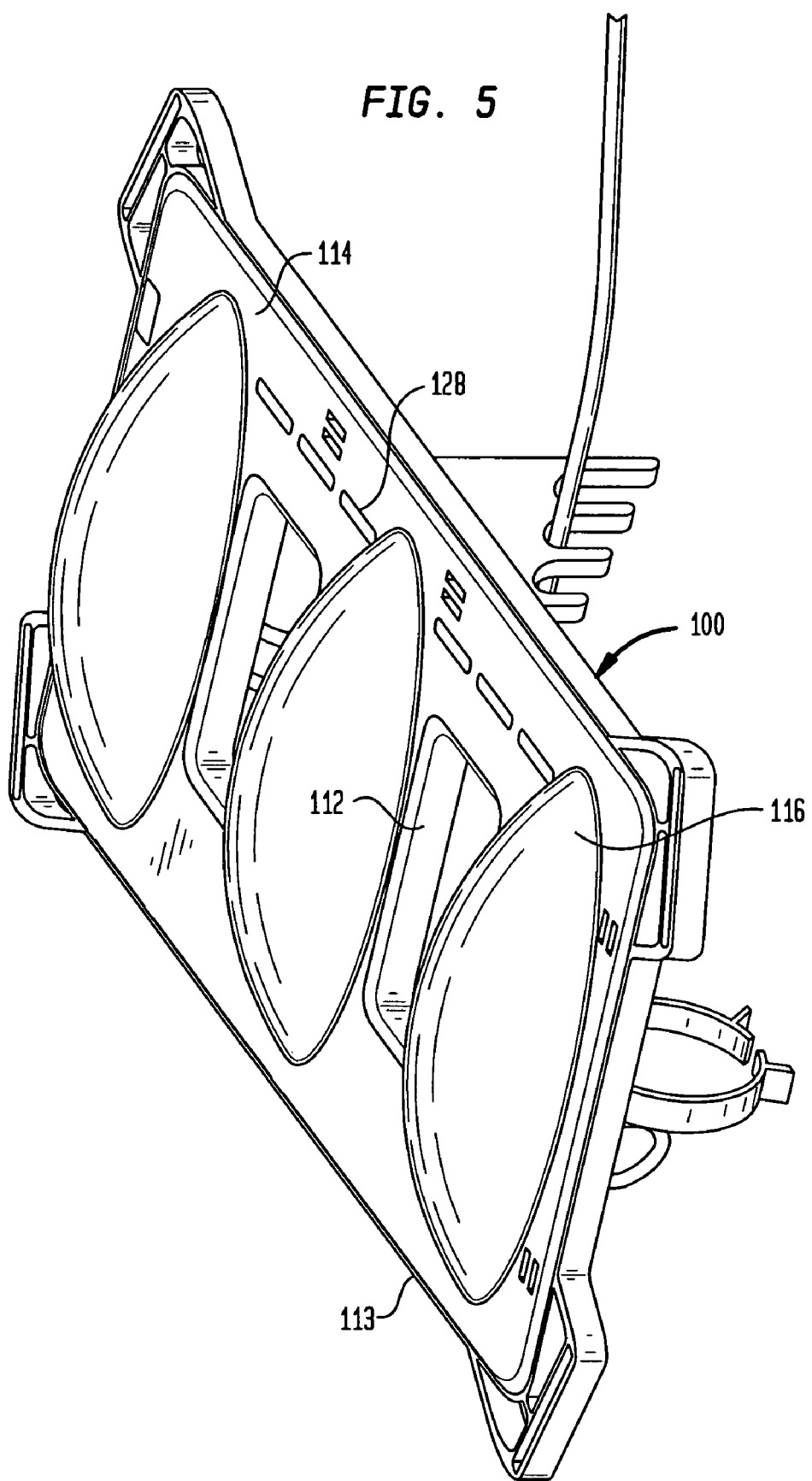
FIG. 5 is a perspective view of the underside of a surgical instrument positioning system in accordance with one embodiment of the present invention.

The void area 101 may be filled with a cushioned underbelly 114 as shown in FIG. 5, depicting a perspective view of the underside of the belt assembly 100. The cushioned underbelly 114 may be attached to the belt assembly 100 by chemical means, such as glue, or mechanical means such as hook and loop type fasteners, belts or screws. Other means, chemical, mechanical, or otherwise, may also be used.

As stated, FIG. 5 depicts a perspective view of the underside of the belt assembly 100 where the void area 101 is generally filled by cushioned underbelly 114. The cushioned underbelly 114 generally contacts the patient so the plastic belt assembly 100 does not. As such, the cushioned underbelly 114 is typically formed from rubber, foam, or the like, for greater patient comfort. The underbelly 114 may also include a bladder 116 filled with air or other fluid to further cushion the belt assembly 100 from the patient. In the embodiment depicted in FIG. 5, three such bladders 116 are shown. Of course, varying numbers of bladders may be utilized depending on the final configuration of the belt assembly 100. The cushioned underbelly 114 typically extends beyond the bottom edge 113 of the skirt 112 such that the skirt 112 does not contact the patient, as shown more clearly in FIG. 4a.

Referring back to FIG. 4, it will be appreciated that the belt assembly 100 includes support protrusions 120 at the intersections of the two side edges 102, 104 with the cephalad edge 106 and caudad edge 108 for the attachment of securement straps (not shown). The support protrusions 120 include elongated openings 122 through which the securement straps may be placed. The openings 122 may be completely enclosed within the support protrusion 120, such as shown with respect to openings 24 in FIG. 1, or may be partially enclosed to form a slot 124 as shown in FIG. 4. The skirted area 112 near the slot 124 may include a built-up shoulder 126 for additional support in preventing the belt assembly 100 from breaking. It will be appreciated that the slot 124 may be provided to permit the attachment of securement straps which have a closed loop at their free end, rather than open ended straps. Open ended straps are typically used with closed openings 24, such as shown in FIG. 1, but may also be utilized in conjunction with slotted openings. Typically, the securement straps will be non-elastic, but will include adjustment means to ensure that the belt apparatus is held tight against the patient. An example of securement straps 300 securing a belt assembly 100 to an operating table is shown in FIG. 3.

The belt assembly 100 depicted in FIG. 4 includes shaped openings 128 forming receptacles or docking sites for the mounting of optional accessories. The receptacles 128 are configured to receive these optional accessories by various means. For example, they may be sized and shaped such that a custom accessory may fit therein in a simple pressure-type fitting. Other accessories may snap in place by utilizing the bottom edge 137 of the skirt 112, or an aperture (not shown) provided in the skirt. The shaped openings 128 may not be provided with a skirt 112, if so desired. Specific examples of bases adapted to dock within the docking sites or receptacles 128 are presented hereinafter.

In addition to the receptacles 128, hooks 130 or loops 132 may also be provided for the attachment of optional accessories. The hooks 130 and loops 132 may include apertures 134 within the belt assembly 100 and the cushioned underbelly 114. The hooks 130 and loops 132 are typically utilized to secure the various lines used in the operating field. As shown in FIG. 5, the cushioned underbelly 114 may be shaped in registration with the various openings 128, 134 of the belt assembly 100.

Figure 6:
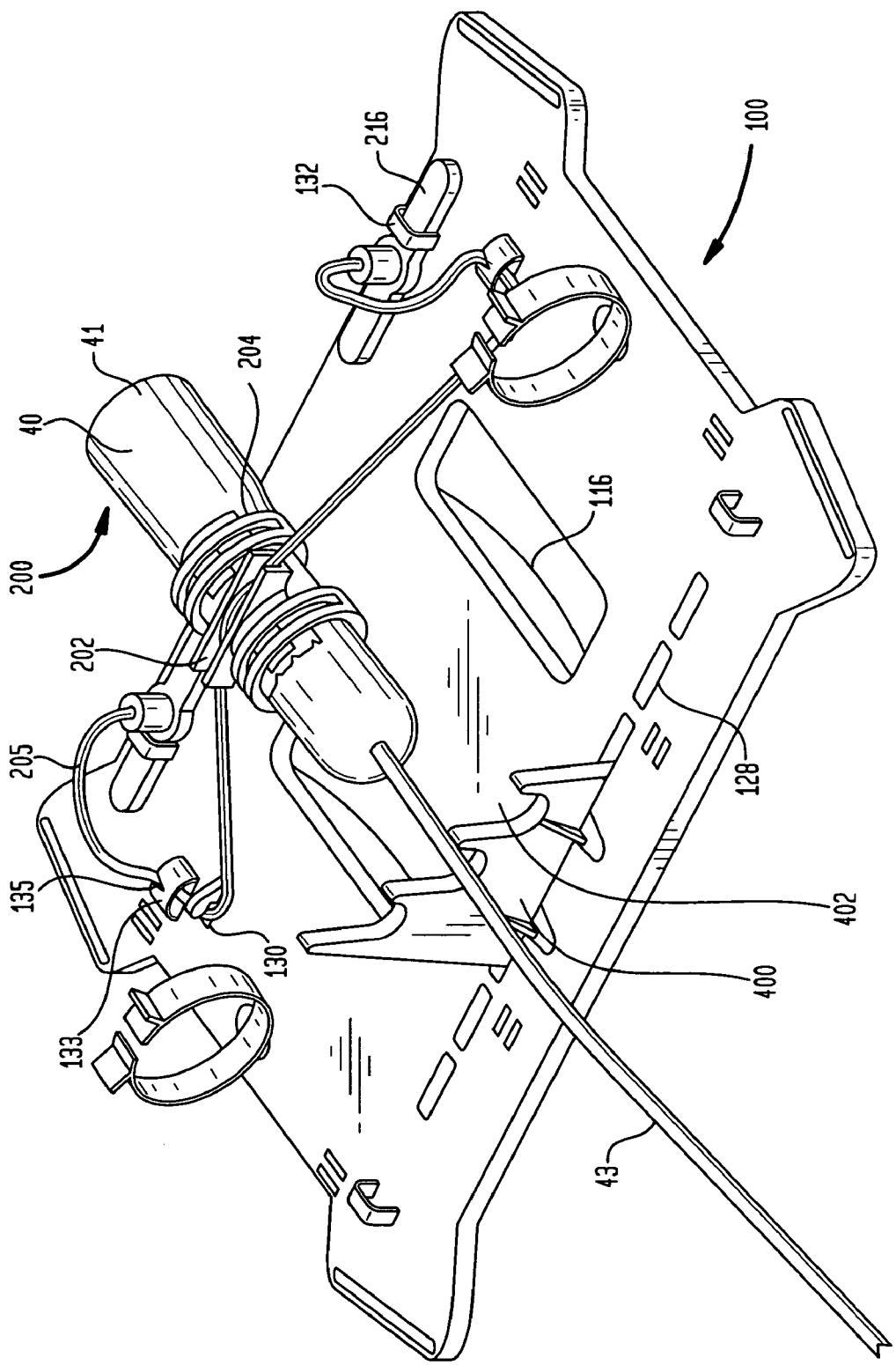
FIG. 6 is a perspective view of a surgical instrument positioning system in accordance with one embodiment of the present invention.

FIG. 6 depicts a retractor holding accessory typically utilized with belt assembly 100. This particular retractor holding assembly is an anti-rotational retractor retention system 200. The anti-rotational retractor retention system 200 is designed to accommodate any current commercially available laparoscopic tissue retractor 40. The retention system 200 is designed to assist with securing the retractor 40 to the belt assembly 100, as the retractor "floats" above the belt assembly 100. The retention system 200 also permits selected rotation of the retractor 40. Once rotated into position, the retractor 40 may be locked down by the retention system 200 such that further rotation may not be achieved until such time as the lockdown system is manually adjusted.

Figure 7:
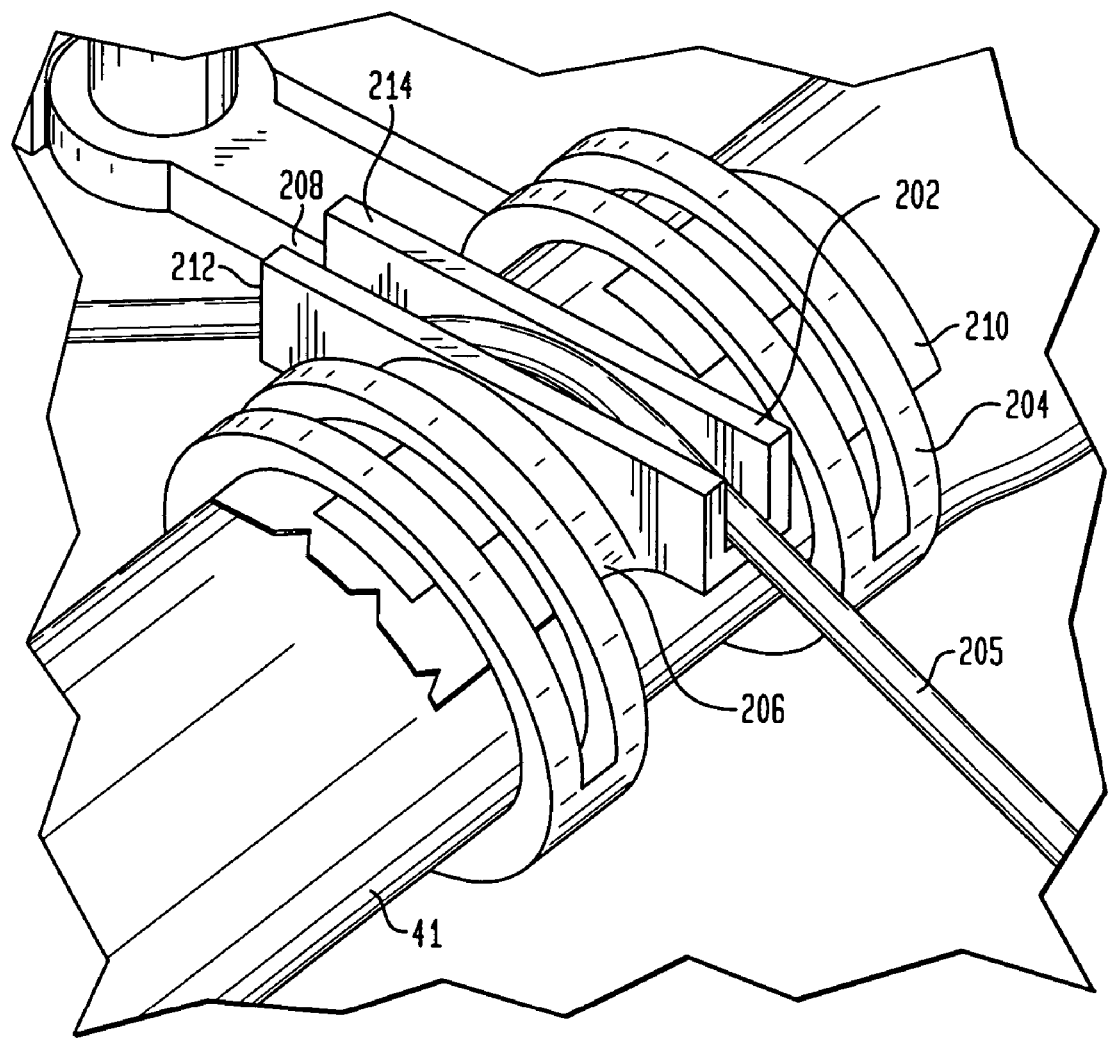
FIG. 7 is a close-up perspective view of a portion of the surgical instrument positioning system of FIG. 6.

As shown in FIGS. 6 and 7, the anti-rotational retractor retention system 200 comprises a saddle 202 and straps 204. Positioning of the anti-rotational retractor retention system 200 is achieved by means of a pulley cord 205. The anti-rotational retractor retention system is stabilized by a height adjustment module 400.

The saddle 202 is typically formed from plastic and comprises a first extension 206, and second extension 210, with a walled portion 208 therebetween. The first extension 206 and second extension 210 are relatively thin sheets molded along an arcuate path approximately matching the diameter of a typical retractor handle 41, as found in the industry. The extensions 206, 210 are typically formed from plastic, and may bend to some degree to accommodate varying handle 41 diameters.

Straps 204 secure the first 206 and second 210 extensions of the saddle 202 to the retractor handle 41, and prevent rotation between the saddle and the handle. The straps 204 are typically formed from elastic, non-slippery material so as to provide tension to secure the saddle 202 against the handle 41 without permitting any slipping. Many types of straps may be utilized. One type of strap is shown in FIG. 7a. In this embodiment, the strap 204' is formed from elastic, non-slippery material. The strap 204' comprises a securement member 211 and at least one aperture 207. The strap 204' may be stretched and placed around either the first portion 206 or the second portion 210 of the saddle 202, and the retractor handle 41. By stretching the strap 204', tension is built up therein. A securement member 211, elevated above the strap by an extension member 213, may then be inserted into an aperture 207 and the strap 204' released. Preferably, the strap 204' will retain enough tension to ensure that the handle 41 is frictionally engaged against the respective portion 206, 210 of the saddle 202. It will be appreciated that the securement member 211 may be bulbous, as shown in FIG. 7a, or configured in other manners such as in the disc-like securement member 211' shown in FIG. 7b, which operates in a like manner.

The walled portion 208 comprises two walls 212, 214, or built-up shoulders, which serve as boundaries between which the pulley cord 205 runs. A portion of the pulley cord 205 is secured within the two walls 212, 214 such that the pulley cord may not slide with respect to the saddle 202. The preferred method of securing the pulley cord 205 to the saddle 202 is by friction of the pulley cord between the walls 212, 214. Preferably, the walls 212, 214 are formed such that the distance between them is approximately equal to, or slightly less than, the diameter of the pulley cord 205. The pulley cord 205 may be inserted between the two walls 212, 214, where it will be retained by friction. The attachment of the pulley cord 205 between the two walls 212, 214 is typically conducted in a controlled environment during the manufacturing process so a strong connection is ensured. However, it may also be accomplished by the surgical staff in preparation for the surgical process.

The pulley cord 205 provides positioning for the retractor holding accessory by shifting of the pulley cord about the belt assembly 100. Specially configured pulley cord holders 133 may be utilized to secure the pulley cord 205 to the belt assembly 100. The pulley cord holders 133 may be loops which include a V-shaped notch 135 within which the pulley cord 205 may be deposited. When fully inserted into such a V-shaped notch, friction will hold the pulley cord 205 in place. The pulley cord 205 may also be partially secured by pulley adjustment hooks 130 or loops 132. The hooks 130 and loops 132 may also be used for other purposes besides securing the pulley cord 205, such as for securing other items.

In order to assist with positioning of the pulley cord 205, leverage devices 216 may be utilized at each end of the pulley cord. As shown in FIG. 6, such leverage devices 216 may be handles. When not in use, the leverage devices 216 may be deposited onto the belt assembly 100 using loops 132 configured for such a purpose. When so placed, they will be held against the belt assembly 100 so as to be inconspicuous in the operating field.

The retractor holding accessory may also be provided with a height adjustment module to stabilize the retractor 40. A typical height adjustment module is shown in FIG. 6 as element 400. The height adjustment module 400 supports the retractor shaft 43 so that the shaft may remain in a desired position and a desired angle. Typically, the height adjustment module 400 contains a plurality of adjustment positions, each defined by U-shaped cutouts 402 of varying heights. The width of the U-shaped cutouts 402 are sized in accordance with the typical sizes of retractors 40 used in the industry.

As is shown in FIG. 6, placing the retractor shaft 43 in the appropriate U-shaped cutout 402 permits the retractor handle 41 to "float" above the surface of the belt assembly 100, supported only by the tension of the pulley cords 205, height adjustment module 400, and insertion point in the patient. To properly align the appropriate U-shaped cutout 402 with the retractor shaft 43, the height adjustment module may be detached and reattached to the belt assembly 100 at predetermined positions corresponding to receptacles 128 provided in the belt assembly. In other embodiments, the height adjustment module 402 may be slid within a groove or channel provided in the belt assembly.

In use, a retractor 40 is placed into the surgical opening of the patient at a proper position and rotation angle to retract the identified organ. The saddle 202 is then placed on the retractor handle 41 and secured in place with straps 204. The height adjustment module 400 is then positioned on the belt assembly 100. The shaft 43 is then inserted into an appropriate U-shaped cutout 402 on the height adjustment module 400. Finally, the anti-rotation assembly 200 is retained in position by securing the pulley cords 205 to the platform 100, by utilizing V-shaped notches 135 of card holders 133. Once in place, the retractor holding accessory will be self-stabilized, and will generally require little to no adjustment throughout the surgical procedure. Notwithstanding the operational order presented, it is to be understood that the steps listed may be conducted in varying sequences without affecting the operation of the retractor holding accessory. It is also to be understood that the retractor holding accessory may be utilized with the single panel belt assembly 100 or the multiple panel belt assembly 10.

As previously discussed, the belt assembly 100 is typically secured to the operating table using securement straps. A typical example of a securement strap is shown in perspective view in FIG. 8. As is shown, the securement strap 300 may include an adjustable fabric strap 302 connected to a velcro strap 304 on its first end 305 and a hook 306 on its second end 307. Typically, the velcro strap 304 is utilized to connect the securement strap 300 to the support protrusions 21, 121 of the belt assembly 10, 100. The velcro strap 304 includes a first end 310 and a second end 312. Each end 310, 312 is covered with corresponding hook and loop type fasteners so they will engage each other securely when pressed together.

In order to connect to the belt assembly 10, 100, the ends 310, 312 may be temporarily separated from each other. One of the ends 310, 312 may then be placed through the elongated opening 24, 122 and reattached to the other end 310, 312, so as to loop through and around the elongated opening. The hook 306 then attaches to a ledge provided on the operating table as is described in U.S. Pat. No. 5,728, 047, or as otherwise known in the art and shown in FIG. 3. Adjustment of the securement strap 300 tension is achieved by way of a buckle 308 provided therefore. Other adjustment apparatuses, such as D-ring assemblies, may also be utilized.

Referring now to FIGS. 10A through 10F, there are shown a number of additional attachment mechanisms for securing the retractor 40, or other device, to the belt assembly 10, 100 that may be used in accordance with the present invention in addition to the anti-rotation retractor retention system 200 previously discussed. It should be appreciated that these embodiments can be used by themselves or in combination with each other or the anti-rotation retractor retention system 200 on a single belt. Each of these additional attachment mechanisms may be used with a single panel belt assembly or multiple panel belt assembly. In FIGS. 10A through 10I, the belt assemblies have been identified as elements 500, 510, 520, 530, 540, 550, 560, 570 and 580. In addition, although reference may be made to a particular medical instrument, such as a retractor 40, it is to be understood that many different instruments may be utilized with the attachment mechanisms described herein.

As shown in FIG. 10A, one embodiment of belt assembly 500 contains a number of raised ridge members 502 which form a plurality of slots 504 therebetween. In this embodiment, the retractor 40 can be slipped into the closest slot 504 once the proper retraction is attained by the surgeon. In this scenario, the end of the retractor insertable into the slots 504 constitutes the attachment portion of the instrument. The attachment portion of the instrument, therefore, need not necessarily include any type of clip or hook and may simply comprise the distal end portion of the instrument. The material forming belt assembly 500 can comprise foam rubber or other high frictional material such that the end of the surgical instrument is held in place and will not slip once inserted into a desired slot 504. These slots can be provided at an angle to better accommodate the angled position of the retractor 40 when in position. Alternatively, a rear wall can be added behind the slots 504 to prevent lateral movement of the end of the surgical instrument.

Similarly, as shown in FIG. 10B, the belt assembly 510 can include a plurality of loop members creating a plurality of corresponding orifices 514 into which the end of the retractor 40 can be inserted for holding the instrument in place during the surgical procedure. These loops can also be closed along the back edge such that they can receive and urge forward a retractor 40.

Referring now to FIG. 10C, another possible embodiment of the belt assembly 10, 100 is shown, in which a plurality of fastening strings 521, 522 are provided to tie over the end of a surgical instrument 525. The surgical instrument 525 can also include one or more annular slots 526 which the strings can fit into to help hold the instrument in place. Alternatively, the fastening strings can be replaced with fastening straps which can include straps attachable by hook and loop type fasteners, buckles, snaps, etc.

A further possible embodiment is shown in FIG. 10D in which the belt assembly 530 includes a lower portion 531 intended to fit over the abdomen of the patient and a rear wall 532 which projects upward from the lower portion 531. Rear wall 532 includes a plurality of raised ridges 533 creating a number of abutment surfaces 534 therebetween. This embodiment is especially useful when the surgeon is performing a surgical procedure in which a ratched grasper 535 is used to provide forward traction to an internal organ. With this embodiment, once the surgeon provides the desired forward traction to the internal organ, the end 536 of the grasper 535 is placed into abutment with the nearest desired abutment surface 534. The raised ridges 533 prevent side to side movement of the grasper 535.

The belt assembly 10, 100 of the present invention may comprise a combination of the attachment features as described above. For instance, referring now to FIG. 10E, belt member 540 may include both a rear wall 542 for use with providing forward traction, and a plurality of post members 543 bridging receptacle 128 for providing attachment positions for an instrument with a clip. In this embodiment rear wall 542 is provided with a number of instrument sockets 541 which are constructed to receive the end of the surgical instrument. Furthermore, rear wall 542 can be lockingly adjustable in the forward and backward direction (along the direction of arrow A) such that in the event that the end of the instrument is pushed to a position more forward than the initial position of the rear wall 542, the rear wall can be moved forward to accommodate the desired forward position of the instrument. The instrument sockets 541 may be cylindrical, as shown, to accept cylindrical medical instruments or may be configured to other desirable shapes.

In the embodiment shown in FIG. 10F, the belt assembly 550 can include lower portion 551 and a rear wall 552 where the outer surfaces 553 and 554 may be covered with hook and loop type fasteners. In this case, the end portion of the surgical instrument can likewise be provided with corresponding loops or hooks so that the instrument can be removably attached to the belt assembly in any desired position.

Alternatively, the handle 41 of the retractor may be covered with a wrap of hook and loop type fastening material. A typical hook and loop wrap is shown in FIG. 9 as element 250. The wrap 250 may be formed as a single sheet of material. A first side (not shown) is typically covered with either male or female hook and loop fasteners. On the second side 252, corresponding hook and loop fasteners may be provided on a portion of the surface so that when wrapped around the retractor handle 41, the two surfaces will mate and become connected. Silicone or rubberized material may be coated on the remaining portion of the second side 252 to increase friction between the retractor handle 41 and the wrap 250. The wrap 250 may then be secured to the belt assembly 550 by hook and loop fasteners such as shown in FIG. 10F, or with straps or other securing means.

In the embodiment of FIG. 10G, the belt assembly 560 can include a plurality of post members 562 bridging a receptacle 128 for providing attachment positions for an instrument with a clip. In this embodiment, however, the belt assembly is also provided with a number of instrument slots 564 which are constructed to frictionally receive and retain the scissors-like handle 565 of a typical 5 mm laparoscopic grasper 566, or other similarly configured instrument.

In the embodiment of FIG. 10H, the belt assembly 570 can include a plurality of post members 572 bridging receptacle 128 for providing attachment positions for an instrument with a clip. In this embodiment, however, the belt assembly can also be provided with one or more post members 574, positionally adjustable within slot 573, to frictionally receive and retain the scissors-like or circular handle 575 of a typical 5 mm laparoscopic grasper 576 disposed around the post member.

Figure 10:
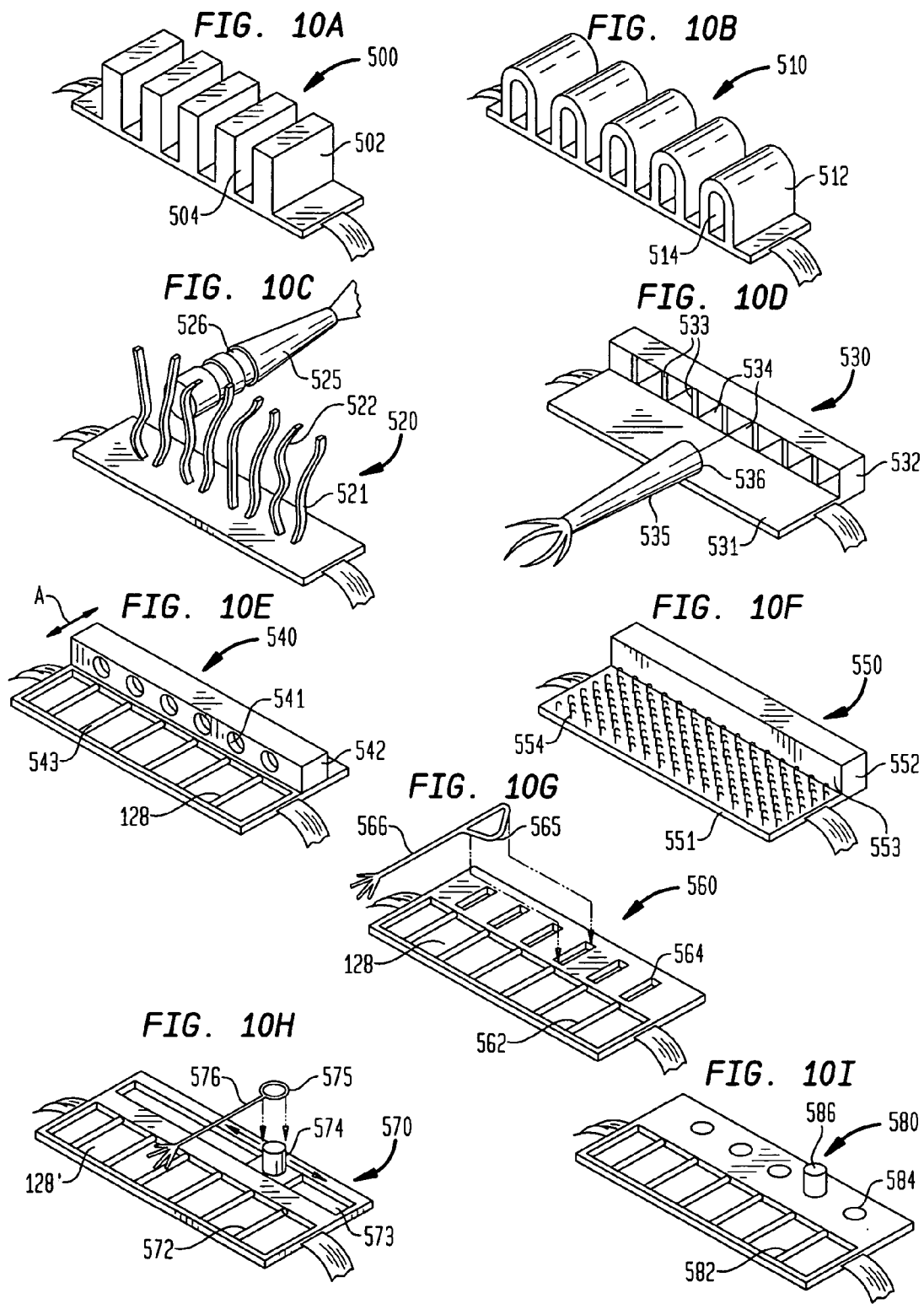
FIGS. 10A through 10I are perspective views of various attachment mechanisms forming portions of the surgical instrument positioning system in accordance with certain embodiments of the present invention.

Alternatively, such as in the embodiment of FIG. 10, a plurality of post-receiving holes 584 can be formed within belt assembly 580 in addition to post members 582. A plurality of posts 586 can be provided for each respective hole 584 or a single, removable post 586 can be used for replacement into the appropriate hole once the desired retraction position is reached, such that the scissors-like or circular handle of a grasper can be retained around the post member.

It should be readily apparent to those skilled in the art that almost any type of attachment method or device can be used to attach the surgical instrument to the belt assembly in accordance with the present invention. For instance, other such attachment means could include pegs projecting from the belt which can fit into one or more holes in the surgical instrument, interlocking belt members which can be closed upon one another with the surgical instrument sandwiched therebetween at the proper position, small clips provided on the belt assembly for clipping into place the surgical instrument, etc. In addition, any of the attachment systems or mechanisms disclosed herein can be used with the belt assemblies disclosed herein, whether single platform or modular belt assemblies.

As previously discussed, the belt assembly 10, 100 may be provided with shaped openings 128 forming receptacles or docking sites for the addition of optional accessories. The shaped openings 128, and thus the optional accessories, can be formed to virtually any shaped fitting within the geometric limits of the belt assembly 100. These shapes generally include geometric shapes such as squares and rectangles, but may be non-geometric as well. Preferably, the shape will be such that the accessory may be inserted in more than one orientation. It is also preferable that the shape be non-circular so the accessory will not rotate within the belt. It has been found most advantageous, however, to provide a shaped opening 128 and accessory formed to the general shape shown in FIGS. 11–16. Of course, the use of such an accessory requires a shaped opening 128 configured similarly, and not as shown in FIG. 1 or 4.

Figure 11:
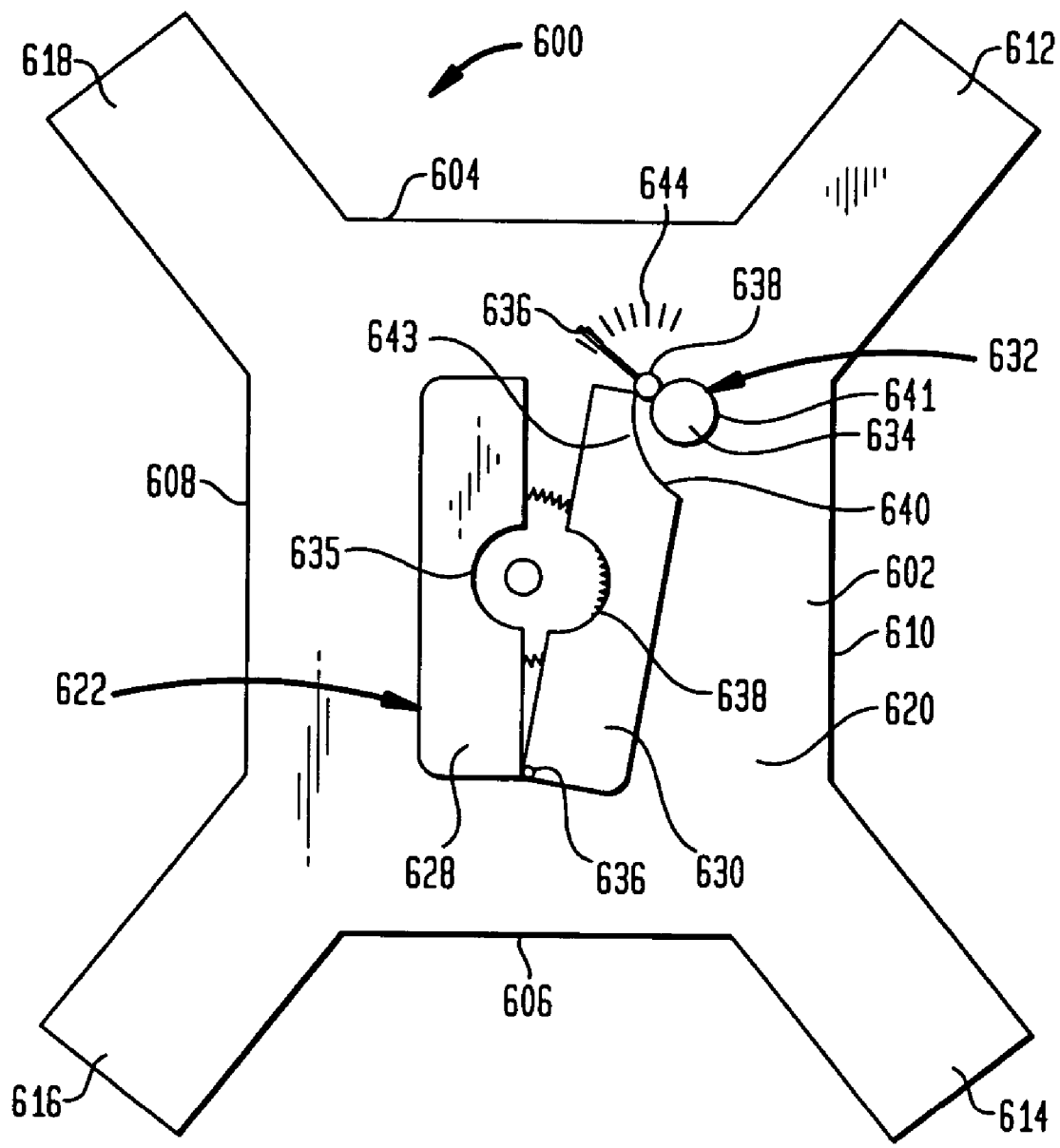
FIG. 11 is a top plan view of a further attachment mechanism forming portions of the surgical instrument positioning system in accordance with certain embodiments of the present invention.

FIG. 11 depicts a top plan view of an accessory 600 for insertion into the shaped opening 128. The accessory is formed into a star-shaped configuration. The main portion 602 of the accessory 600 is relatively square or rectangular, comprising four sides. A first side 604 is oriented parallel to a second side 606. The first side 604 and second side 606 extend between a third side 608 opposed from a fourth side 610. The first side 604 and second side 606 are generally perpendicular to the third side 608 and fourth side 610. Extending radially outward from the center of the main portion 602 are four extension members 612, 614, 616, 618. Each extension member 612, 614, 616, 618 intersects two of the four sides 604, 606, 608, 610, at the point of the main portion 602 where the two sides would have otherwise converged. For example, extension member 612 is located between first side 604 and fourth side 610, as shown in FIG. 11.

The main portion 602 and the extension members 612, 614, 616, 618 are formed in registration with the shaped openings 128 of the belt assembly 10, 100, so the accessory 600 will fit securely within the shaped opening. Because the accessory 600 shown in FIG. 11 is symmetrical, it may be placed within the shaped opening in any one of four orientations, rotated 90° from each other.

A locking apparatus 622 is located on the top surface 620 of the accessory 600. Preferably, the locking apparatus 622 is located near the center of the main portion 602. As shown more clearly in FIG. 12, the locking apparatus 622 is adapted to engage a spherical base 624 of a medical device support 626 to form a ball and socket joint. The locking apparatus 622 is comprised of three major components, a fixed block 628, a rotatable block 630, and a locking mechanism 632.

The fixed block 628 is a generally rectangular member attached to the top surface 620 of the main portion 602 of the accessory 600. The fixed block 628 includes a recessed portion 635 adapted to receive portions of the spherical base 624 of the medical device support 626. This recessed portion 635 is typically cupped to have a diameter slightly larger than the spherical base 624 so as to form a socket. The rotatable block 630 is rotatably engaged with the top surface 620 of the main portion 602 of the accessory 600. A pin 636 extends through the corner 631 of the rotatable block 630 nearest the fixed block 628. The pin 636 is recessed into the top surface 620 of the accessory 600 by means sufficient to support the rotatable block 630 upon the top surface while permitting the rotatable block to pivot about the longitudinal axis of the pin.

As with the fixed block 628, the rotatable block 630 also includes a recessed portion 638 adapted to engage portions of the spherical base 624 of the medical device support 626. This recessed portion 638 is also cupped to form a socket. The rotatable block 630 also includes a bearing surface 640 upon which the locking mechanism 632 acts. The bearing surface 640 is preferably arcuate and is generally positioned in a corner 643 opposite to that of the pin 636.

As best shown with reference back to FIG. 11, the locking mechanism 632 comprises a cylinder 634 and a locking arm 636 connected by a rotation member 638. The cylinder 634 is connected to the rotation member 638 at a single point along the cylinder's outside wall 641. The locking arm 636 extends from the rotation member 638 away from the cylinder 634. Movement of the locking arm 636 rotates the cylinder 634 about the rotation member 638 such that the outside wall 641 of the cylinder contacts the bearing surface 640 of the rotatable block 630. The greater the degree of rotation of the locking arm 636, the greater influence the cylinder 634 has on the bearing surface 640 of the rotatable block 630 and the more the rotatable block rotates about pin 636.

Figure 12:
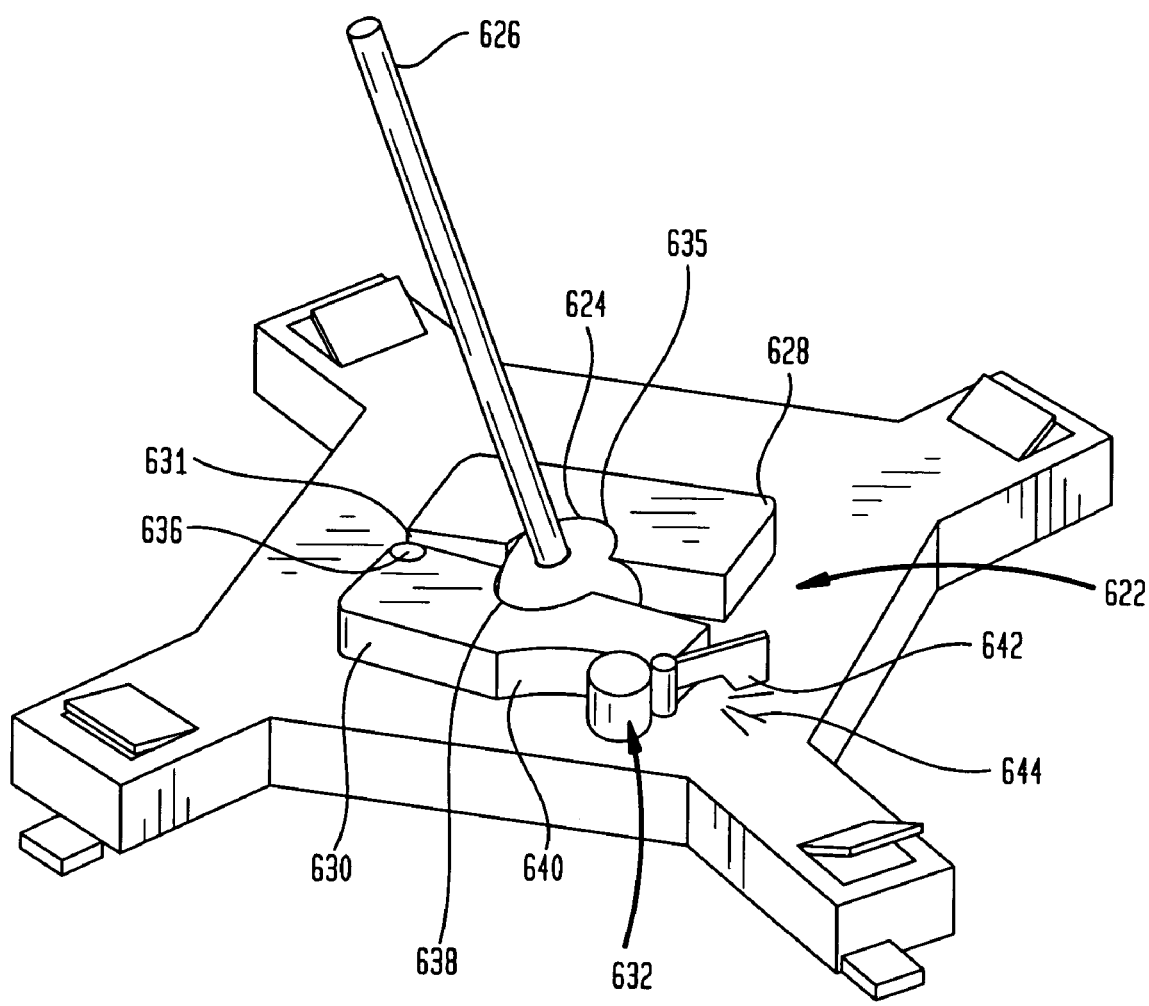
FIG. 12 is a perspective view of the attachment mechanism of FIG. 11.

As shown in FIG. 12, the locking arm 636 is provided with a tabbed member 642 adapted to engage a series of notches 644 provided on the top surface 620 of the accessory 600. When the desired orientation of the rotatable block 630 is met, the tabbed member 642 may be placed within a notch 644 such that the rotation will become fixed until the operator of the device releases the tabbed member from the notch. Preferably, a sufficient number of notches 644 are provided on the top surface 620 to permit a wide range of locking positions.

It will be appreciated that rotation of the cylinder 634 influences rotation of the rotatable block 630 due to the interaction of the cylinder outside wall 641 and the bearing surface 640. Like the lobe of a cam shaft, as the cylinder 634 rotates, the portion of the outside wall 641 contacting the bearing surface 640 increases in distance away from the rotation member 638. The rotation angle of the rotatable block 630 is proportional to this distance.

In operation, the spherical base 624 of a medical device support 626 may be placed between the fixed block 628 and the rotatable block 630 within the recessed portions 635, 638. The top surface 620 of the accessory 600 may also include a recess (not shown) in which the spherical base 624 of the medical device support 626 may lie. Once the spherical base 624 of the medical device support 626 is so placed, rotation of the locking mechanism will cause the rotatable block 630 to progressively squeeze the spherical base 624 such that it is retained in a friction fit between the fixed block 628, rotatable block 630, and top surface recess (not shown). Depending on the size of the spherical base 624 and the friction force required, the tabbed member 642 may be placed in a notch 644 appropriate for the compression force desired. It will be appreciated that a high compressive force will retain the spherical base 624 without permitting any deflection or rotation while a lesser compressive force will retain the spherical base in a fixed position, but may still permit selective deflection or rotation thereof, without a great deal of effort. Either support technique may be preferred, depending on the apparatus being supported and its intended use in the operative arena.

The rotatable block 630, fixed block 628 and spherical base 624 are typically formed from plastic. Other materials, such as hard rubberized material or injection molded material, may also be used. Rubberized materials are advantageous as the coefficient of friction between rubberized materials is greater than that of smooth plastic materials. It will be appreciated that the spherical base 624 of the medical device support 626, the recessed portion 635 of the fixed block 628, the recessed portion 638 of the rotatable block 630, and the recessed portion (not shown) of the top surface 620 may be knurled, dimpled or otherwise roughened to increase the coefficient of friction between the elements.

Figure 13:
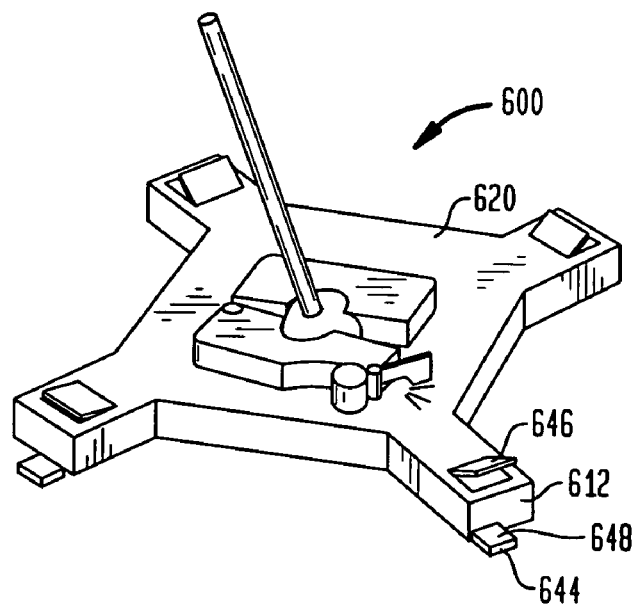
FIG. 13 is an additional perspective view of the attachment mechanism of FIG. 11.

Each extension member 612, 614, 616, 618 of the accessory 600 may be provided with locking toe members to help stabilize the base once inserted into the belt assembly 10, 100. As shown in FIG. 13 and with reference to extension member 612 in particular, a toe member 644 may extend from the bottom surface (not shown) of the accessory 600 along the longitudinal axis of the extension member 612 radiating outward from the center of the accessory 600. It will be appreciated that the toe member 644 extends beyond the limit of the extension member 612. On the top surface 620 of the extension member 612, there may be provided a release mechanism 646 for selectively extending and retracting the toe member 644 from the extension member 612. Preferably, the toe member will automatically retract upon application of an upward force, such as when installing the accessory 600 into the belt assembly 10, 100 from a position above the assembly, but not retract upon application of a downward force, such as when removing the accessory from the belt assembly.

To install the accessory 600 into the belt assembly 10, 100, the release mechanism 646 is typically depressed, wherein the toe member 644 will retract into the retention member 612. Once the extension member 612 has been placed into the belt assembly 10, 100, the release mechanism 646 may be released, permitting the toe member to extend out toward its unmanipulated position. The toe member 644 may also be constructed such that it will self-retract when the accessory 600 is placed within the belt assembly 10, 100, but will not self-retract upon attempted removal of the accessory from the belt assembly. Once installed, the upper surface 648 of the toe member 644 will then bear against the bottom surface (not shown) of the belt 10, 100 while the bottom surface (not shown) of the toe member bears against the cushioned underbelly 114. If shaped opening 128 is provided with a skirt 112, the upper surface 148 of the toe member 644 may bear against the bottom edge 113 of the skirt. Following this procedure on each of the four extension members 612, 614, 616, 618 will result in the accessory 600 being retained within the belt assembly until such time as each of the release mechanisms 646 are manipulated to remove the accessory 600 from within the belt assembly 10, 100.

The accessory 600 may also be supported by the bladder 116 (FIG. 5). Resting the accessory 600 on the bladder is sufficient to secure the accessory 600 because the largest forces on the accessory are typically those pulling the accessory out of the belt 10, 100, not pushing it further in. In other embodiments, the accessory may rest directly on the patient.

As previously stated, the accessory 600 is provided as a support for various medical devices. FIG. 12 depicts preferable elements of each of these medical devices. These elements include the spherical base 624 and the medical device support 626. Because of the nature of the ball and socket joint created by the spherical base 624 in the locking apparatus 622, the medical device mounted on the accessory 600 may be rotated through a full 360°, as well as deflected through an approximately 180° angle. It will be appreciated that this 180° deflection angle is limited in part by the interference between the medical device support 626 and the top surface of either the fixed block 628 or the rotatable block 630. For example, the maximum angle achievable over the fixed block 628 and the rotatable block 630 is when measured between the interference of the medical device support 626 and the fixed block and the interference of the medical device support and the rotatable block. It will be appreciated that the greatest angle achievable is one in which the medical device support 626, falls between the gap formed between the fixed block 628 and the rotatable block 630. In addition, it will be appreciated that larger diameter spherical bases 624 permit greater angles of deflection than smaller diameter spherical bases, as the exit point of the medical device support 626 from the spherical base 624 will be higher above the top surface of the fixed block 628 and rotatable block 630 in the case of a large sphere.

Figure 14:
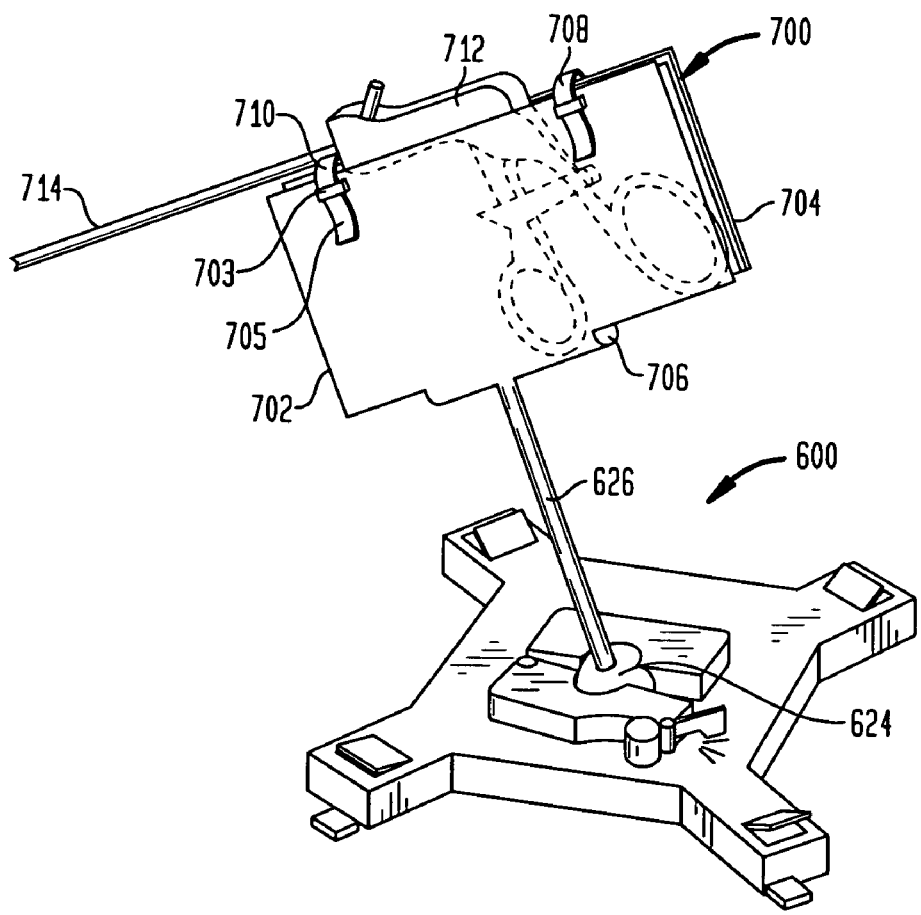
FIG. 14 is a perspective view of the attachment mechanism of FIG. 11 including a support clamp attachment.

FIG. 14 depicts one example of a medical device support of the present invention. This particular medical device support is a clamp support 700. As shown in FIG. 14, the clamp support 700 comprises a first cover 702 and a second cover 704 connected by a spine 706 on one end of each cover. The opposite end of each cover includes straps 708, 710. The straps 708, 710, may include traditional clasps or other locking devices such as buckles, D-rings, hook and loop fasteners, or the like. Each of the two covers incorporate elements of the straps 708, 710 which are complimentary, but not necessarily identical. For example, first cover 702 may contain buckle 703 while second cover 704 contains the complimentary strap 705.

The medical device support 626, previously discussed, is connected to the spine 706 such that the entire support 700 may rotate 3600 or be deflected through various angles. A clamp 712 may be held within the support 700 as shown in FIG. 14. Of course, other medical devices may alternatively be supported therein. It will be appreciated that the clamp of FIG. 14 is shown to be engaging a tube 714 extending from the operative field.

The entire belt assembly including the accessory 600, support 700 and medical device such as the clamp 712, shown in FIG. 14, is designed to eliminate the need for additional support staff to assist the surgeon during a surgical operation. In use, the belt assembly 10, 100 is laid across the patient and secured in the manner previously described. An accessory 600 having a locking apparatus 622 is then attached to the belt assembly 10, 100. The support 700 with medical device support 626 and spherical base 624 may then be inserted into the locking apparatus 622. Once so inserted, the locking mechanism 632 may be positioned such that a minimal amount of friction is generated between the spherical base 624 and the recessed portion 635 of fixed block 628 and the recessed portion 638 of rotatable block 630. This minimal friction should be sufficient to allow the support 700 to be positioned in an upright stance while still permitting selective rotation and deflection of the support.

A medical device such as the clamp 712 shown in FIG. 14 may then be mounted within the support 700, which is secured within the locking apparatus 622 using a minimal amount of friction. Preferably, the clamp 712 has been previously manipulated to clamp the subject object, such as the tube 714 shown in FIG. 14. The clamp 712 may be placed between the first cover 702 and the second cover 704 of the support 700. The covers 702, 704 may then be brought together to squeeze the clamp 712 therebetween. Locking straps 708, 710 may then be positioned to secure the covers in place, thus preventing the clamp from being moved relative to the covers. Once so positioned, the support 700 may be oriented to the desired position wherein the locking mechanism 632 may be further locked to prevent rotation or deflection of the medical device support 626. At this point, the clamp 712 will be secure and the surgeon may continue the operation without fear of movement thereof.

It will be appreciated that the portions of the first cover 702 and the second cover 704 facing each other may be provided with additional materials to assist with the securing of the clamp 712 or other medical device. Such materials include high density foam, rubber coatings, or the like. It is generally preferable that any such material generally used have the qualities of cushioning the clamp 712 or other medical device while also having a relatively high level of friction between the material and the medical device. It is also preferable that the material be somewhat resilient, to assist with preventing sliding of the clamp 712 or other medical device.

Figure 15:
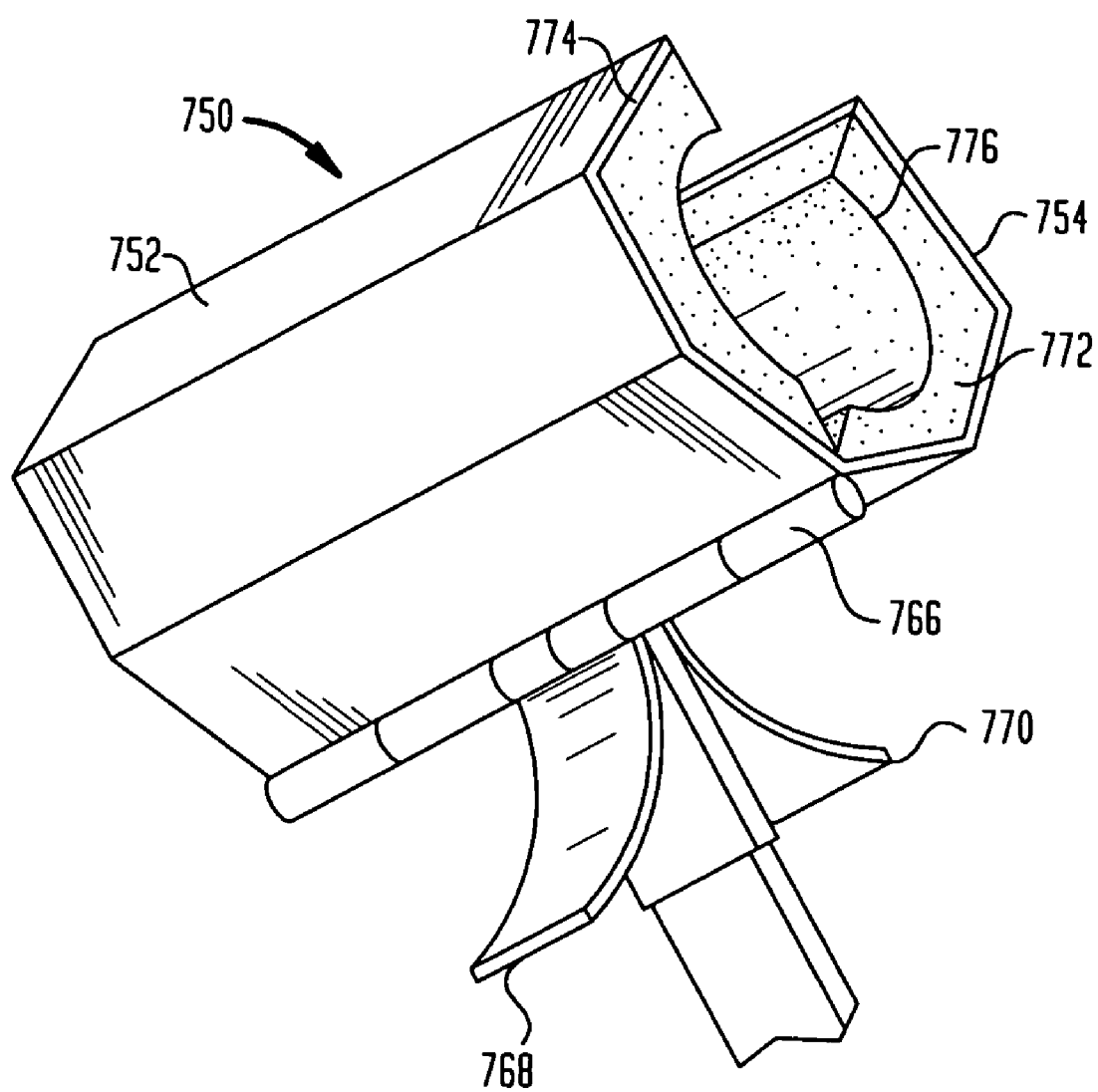
FIG. 15 is a perspective view of a portion of another support clamp attachment capable of being attached to the attachment mechanism of FIG. 11; and, FIG. 16 is a perspective view of a camera support attached to the attachment mechanism of FIG. 11.

Another example of a medical support for use in the present invention is shown in FIG. 15. This particular medical device is a cradle 750. The cradle 750 comprises a first jaw 752 connected to a second jaw 754 by way of a spring hinge 766. The spring hinge 766 is biased such that in its natural state, the first jaw 752 and the second jaw 754 are placed in a closed position in contact with each other such that a medical device may be retained therebetween. In order to open the jaws, the spring hinge 766 is provided with a first leverage member 768 and a second leverage member 770. Each of the leverage members 768, 770 is a generally rectangular flat member having one of its short ends attached to the spring hinge 766 and its opposite end extending outwardly therefrom. Each of these opposite ends on the respective leverage members 768, 770 arch out away from each other, as shown in FIG. 15. When the leverage members 768, 700 are squeezed together, the first jaw 752 and the second jaw 754 spread apart to open against the natural biasing of spring hinge 766.

The first jaw 752 and second jaw 754 may be constructed to many different shapes. Notwithstanding, the jaws 752, 754 shown in FIG. 15 are each three-sided, such that when closed they substantially form a regular hexagon. Various other polygons, arches, or other shapes, either geometric or non-geometric, may also be formed.

As with the support 700, the interior portions of the first jaw 752 and the second jaw 754 may be lined with various materials to assist with the securement of medical accessories. This protective material 772 may be shaped to an interior configuration different from its exterior configuration. As shown in FIG. 15, a cradle 750 may have protective material 772 with an exterior configuration 774 shaped such that it conforms to the three-sided first jaw 752. Meanwhile, the interior configuration 776 may form a semicircle. Other shapes may also be utilized. Preferably, the protective material 772 is constructed such that it cushions the medical accessory to be placed within the cradle 750 while also having sufficient friction to prevent the accessory from sliding relative to the cradle.

Figure 16:
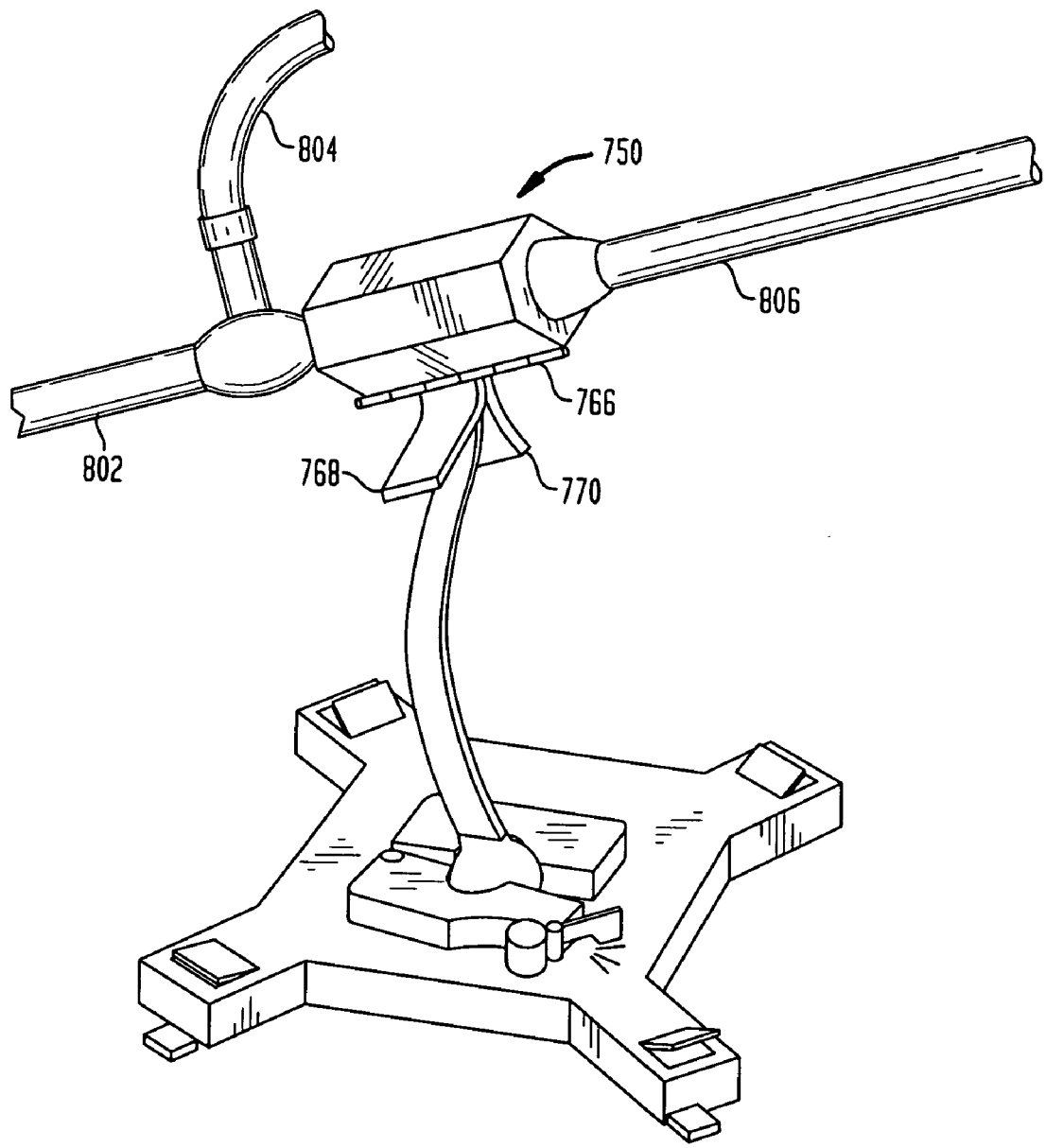

FIG. 16 depicts a camera assembly 800 fully mounted to a cradle 750 as an example of the type of accessory that the cradle may support. In this figure, a camera (not shown) is secured within the cradle 750. A telescope 802 and a light cord 804 extend from one side of the cradle 750 while a camera cover 806 extends from the other. The telescope 802, light cord 804, and camera cover 806 are all common elements known in the industry.

The following table illustrates several of the key features of the present invention. By no means is this table to be considered as complete, exhaustive, or in any way limiting of the features of the present invention.

Modular Design
a) enables broadening of the range of laparoscopic retraction;
b) provides varying widths to accommodate a patient's girth;
c) longitudinal platform module makes it possible to position instruments intended to displace tissue or organs in a direction at right angles to that achievable with the previous design.

A. Interlocking Modules
a) allows retraction by positioned instruments dependent on the orientation of the slots and rungs of the individual modules;
b) the mechanism of interlocking is universal so that modules with horizontally disposed struts may be interlocked with similar modules or with modules having vertically directed struts to form a belt;
c) the constructions or modules may be fixed by rods which are disposed through the interdigitalized links;
d) this construction permits the surgeon to customize the instrument positioning device to the patient and the planned procedure;
e) the attachment of the instruments to the positioning device could be
  (i) by hooks attached to straps or the handle of instruments being positioned;
  (ii) by using projections on the instruments;
  (iii) by individual gripping clips which can be applied to the instrument handle;
  (iv) other means disclosed herein;
f) each module may preferably be 10 cm wide and may be formed from molded plastic;
g) the undersurface may be padded with synthetic plastic or foam;
h) the assembly may be secured to the operating table with adjustable length non-elastic straps;
i) the end pieces may be designed to provide for attachment of these adjustable table straps which may fix the composite belt to the operating room table;
  1. Platform Design
  a) a single platform may be used in lieu of interlocking modules;
  b) platforms may be sized for use with patients of varying girth;
  c) the platform may be secured to the operating table by adjustable non-elastic straps.
  2. Retractor Holding Accessory
  a) Anti-Rotational Device
    i) the anti-rotation device may be used effectively with all currently marketed laparoscopic tissue retractors;
    ii) the anti-rotation device may be strapped to the retractor handle so as to saddle the handle;
  b) Positioning System
    i) a pulley system may be positioned over the saddle to position the retractor and help to control rotation;
    ii) the pulley system may be adjusted to maintain retraction by changing the lengths of pulley cord to the right and left of the anti-rotation device.
    iii) the straps of the pulley system may be securely fastened using an adjustment buckle located on the platform;
    iv) the straps may include handles to assist with leveraging;
    v) when not in use, these handles may be housed in slots provided therefor on the platform.
  c) Stabilization System
    i) a pivot wedge may be placed under the retractor handle or shaft so that the handle or shaft passes through a notch with the appropriate height for the individual patient's abdominal girth;
    ii) the pivot wedge may be inserted into various receiving points on the platform coinciding with the location of the positioning system and surgical entry point.
  3. General Features of Belt Assembly
  a) detachable rings or straps may be used to organize a laparoscopic camera, light cords or other lines entering operative field;
  b) once positioned, the instrument and all appurtenances will remain in position even with changes in the operating room table position, such as to the reversed Trendelenberg position;
  c) a telescope and camera cradle attachment may also be provided to fit within docking sites provided therefor on the platform;
  d) the system may include tissue grasper holders or other accessories adapted to be inserted into docking sites provided on the belt assembly.
  4. General Features of Docking Sites
  a) provide versatility in that a single belt design may utilize various docking site accessories such as a telescope base or a camera cradle base, among others;
  b) may be provided with locking grips for stabilization within the base;
  d) permit reuse of the docking site accessories even if the belt is disposable; symmetrical shape permits the docking site accessory to be installed with multiple orientations.

Although the invention herein has been described with reference to particular embodiments, it is to be understood that these embodiments are merely illustrative of the principals and applications of the present invention. It is therefore to be understood that numerous modifications may be made to the illustrative embodiments and that other arrangements may be devised without departing from the spirit and scope of the present invention.

The invention claimed is:

1. A positioning system for use during surgical procedures comprising a belt assembly positionable about a bodily surface of a patient, said belt assembly comprising a platform and a surgical instrument retention system, said surgical instrument retention system comprising a saddle adapted to be positioned on a surgical instrument, straps adapted to secure said saddle to the surgical instrument, and a pulley cord coupled to said saddle so as to selectively position the surgical instrument upon movement of said pulley cord, said surgical instrument retention system adapted to restrain movement of the surgical instrument.

2. The positioning system of claim 1, further comprising securement straps for securing said belt assembly to an operating table during the surgical procedure, said securement straps having a first end attached to said belt assembly and a second end attached to said operating table.

3. The positioning system of claim 1, wherein said platform further comprises elements for securing said pulley cords in a desired position, each of said elements including a V-shaped notch wherein said pulley cord may be frictionally retained.

4. The positioning system of claim 1, wherein said platform further comprises a height adjustment module for adjusting the height of the surgical instrument above the level of said platform.

5. The positioning system of claim 4, wherein said height adjustment module includes a plurality of grooves, at least two of said grooves formed to different heights above said platform.

6. The positioning system of claim 1, wherein said platform includes a perimeter edge, said perimeter edge including a skirt extending beyond the platform.

7. The positioning system of claim 6, wherein said platform includes a cushioned underbelly in contact with the patient, said cushioned underbelly partially extending beyond the limits of said skirt.

8. A retention system for retaining a surgical instrument, said retention system comprising a saddle adapted to be positioned on a surgical instrument, straps adapted to secure said saddle to the surgical instrument, and a pulley cord coupled to said saddle so as to selectively position the surgical instrument upon movement of said pulley cord.

9. The retention system of claim 8, wherein said saddle includes a first portion, a second portion, and a walled portion therebetween, said pulley cord being secured within said walled portion.

10. The retention system of claim 9, wherein said walled portion of said saddle comprises two spaced-apart walls connected to each other by a support portion, said pulley cord being retained between the two spaced-apart walls.

11. The retention system of claim 8, further comprising a platform adapted to be positioned about a bodily surface of a patient, wherein said retention system may be connected to said platform via said pulley cord.

12. The retention system of claim 11, wherein said platform includes a pair of elements having V-shaped notches capable of securing said pulley cords therein by friction.

13. The retention system of claim 11, further comprising a height adjustment module engaged with said platform, said height adjustment module adapted to support the surgical instrument above the level of said platform.

14. An instrument positioning system for use during surgical procedures comprising:

a belt assembly adapted to be positioned about a bodily surface of a patient, said belt assembly comprising a platform having a shaped opening for receiving an accessory;

an accessory adapted to fit securely within said shaped opening, said accessory comprising a base having a locking apparatus for locking a medical device to said base;

wherein said locking apparatus comprises a fixed block fixedly engaged to said base, a rotatable block rotatably engaged to said base, and a locking mechanism for selectively rotating and locking said rotatable block.

15. The instrument positioning system of claim 14, wherein said rotatable block is rotated such that a portion of a device may be secured between said rotatable block and said fixed block.

16. The instrument positioning system of claim 14, wherein said locking mechanism comprises an element adapted to bear against said rotatable block to rotate said rotatable block in a progressive manner as said element is rotated.

17. The instrument positioning system of claim 14, wherein a medical device support having a spherical base is fixedly engaged by its spherical base between said rotatable block and said fixed block.

18. The instrument positioning system of claim 17, wherein said medical device may rotate through the full 360 degrees.

19. The instrument positioning system of claim 17, wherein said medical device may be deflected through approximately 180°.

20. The instrument positioning system of claim 14 further comprising a medical device support, said medical device support comprising a spherical base and an elongate stem extending therefrom, said spherical base adapted to be secured between said fixed block and said rotatable block.

21. The instrument positioning system of claim 20, wherein said medical device support further comprises a pair of opposed sides connected by a hinge, said opposed sides being biased toward each other by said hinge.

22. The instrument positioning system of claim 21, wherein said hinge is spring-loaded.

23. The instrument positioning system of claim 21, wherein said opposed sides included padded interior portions adapted to secure a medical instrument without damaging the instrument.

24. A positioning system for use during surgical procedures comprising a belt assembly positionable about a bodily surface of a patient, said belt assembly comprising a platform having a first side and a second side, said first side having a locking apparatus adapted to permit attachment of a surgical instrument thereto, said locking apparatus comprising a fixed block fixedly engaged with said first side, a rotatable block rotatably engaged with said first side, and a locking mechanism for selectively rotating and locking said rotatable block, said second side having a cushion coupled thereto.

* * * * *